US011358937B2

(12) United States Patent
Sleiman et al.

(10) Patent No.: US 11,358,937 B2
(45) Date of Patent: Jun. 14, 2022

(54) REAGENTS BASED ON A TERTIARY AMINE BACKBONE TO INTRODUCE CHEMICAL FUNCTIONALITY IN NUCLEIC ACIDS AND SEQUENCE-CONTROLLED POLYMERS

(71) Applicant: THE ROYAL INSTITUTION FOR THE ADVANCEMENT OF LEARNING/MCGILL UNIVERSITY, Montréal (CA)

(72) Inventors: Hanadi F. Sleiman, Montreal (CA); Donatien De Rochambeau, Montréal (CA); Yuanye Sun, Los Angeles, CA (US)

(73) Assignee: THE ROYAL INSTITUTION FOR THE ADVANCEMENT OF LEARNING/MCGILL UNIVERSITY, Montréal (CA)

( * ) Notice: Subject to any disclaimer, the term of this patent is extended or adjusted under 35 U.S.C. 154(b) by 0 days.

(21) Appl. No.: 17/263,243

(22) PCT Filed: Aug. 9, 2019

(86) PCT No.: PCT/CA2019/051091
§ 371 (c)(1),
(2) Date: Jan. 26, 2021

(87) PCT Pub. No.: WO2020/142825
PCT Pub. Date: Jul. 16, 2020

(65) Prior Publication Data
US 2021/0163422 A1    Jun. 3, 2021

Related U.S. Application Data

(60) Provisional application No. 62/717,181, filed on Aug. 10, 2018.

(51) Int. Cl.
| | | |
|---|---|---|
| *C07D 233/02* | (2006.01) | |
| *C07D 209/08* | (2006.01) | |
| *C07D 249/04* | (2006.01) | |
| *C07D 309/14* | (2006.01) | |
| *C07D 495/04* | (2006.01) | |
| *C12P 19/34* | (2006.01) | |

(52) U.S. Cl.
CPC ......... *C07D 233/02* (2013.01); *C07D 209/08* (2013.01); *C07D 249/04* (2013.01); *C07D 309/14* (2013.01); *C07D 495/04* (2013.01); *C12P 19/34* (2013.01)

(58) Field of Classification Search
None
See application file for complete search history.

(56) References Cited

PUBLICATIONS

Lutz et al. "Defining the field of Sequence-Controlled Polymers", Macromolecular Rapid Communications, 2017, 37, pp. 1-12.
Abselaziz et al. "Synthesis of Non-Natural Sequence-Encoded Polymers Using Phosphoramidite Chemistry", J. Am Chem. Soc. 2015, 5629-5635.
Pongphak et al. "Recent advances in DNA nanotechnology", Current Opinion in Chemical Biology online, May 9, 2018, 46, 63-70.
Edwardson etal. "An Efficient and Modular Route to Sequence-Defined Polymers Appended to DNA". Angewandte Chemie International Edition, 2014, 53, 4567-4571.
Donation et al. "DNA-Teflon Sequence-controlled Polymers". Polymer Chemistry, 2016, 7, 4998-5003.

*Primary Examiner* — Samantha L Shterengarts
(74) *Attorney, Agent, or Firm* — Norton Rose Fulbright LLP

(57) ABSTRACT

It is provided an achiral, non-nucleosidic backbone for phosphoramidites that can be inserted with high yields in nucleic acid strands and sequence-controlled oligo(phosphodiester)s through solid phase synthesis (SPS) using a DNA synthesizer. From this backbone, platforms with useful chemical handles were synthesized, further functionalized, transformed into phosphoramidites and attached to nucleic acid strands and sequence-controlled oligo(phosphodiester)s. The backbone is based on a tertiary amine with a 3-6 carbon spacer between the central nitrogen and the two external hydroxyls. The spacer has been optimized to increase coupling yields and stability.

15 Claims, 6 Drawing Sheets

Specification includes a Sequence Listing.

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Synthesized Sequence

<400> SEQUENCE: 1
tttttcagtt gaccatata                                                    19

<210> SEQ ID NO 2
<211> LENGTH: 14
<212> TYPE: DNA
<213> ORGANISM: Artificial Sequence
<220> FEATURE:
<223> OTHER INFORMATION: Synthesized Sequence

<400> SEQUENCE: 2
cagttgacca tata                                                         14

<210> SEQ ID NO 3
<211> LENGTH: 14
<212> TYPE: DNA
<213> ORGANISM: Artificial Sequence
<220> FEATURE:
<223> OTHER INFORMATION: Synthesized Sequence

<400> SEQUENCE: 3
cagttgacca tata                                                         14

<210> SEQ ID NO 4
<211> LENGTH: 96
<212> TYPE: DNA
<213> ORGANISM: Artificial Sequence
<220> FEATURE:
<223> OTHER INFORMATION: Synthesized Sequence

<400> SEQUENCE: 4
ccacacttgc tttttcctat atggtcaact gctcttttct gaccagtgtc agcaaacctt       60
ttgtagtaat accagatgga gttttgtgt gcgtgc                                  96

REAGENTS BASED ON A TERTIARY AMINE BACKBONE TO INTRODUCE CHEMICAL FUNCTIONALITY IN NUCLEIC ACIDS AND SEQUENCE-CONTROLLED POLYMERS

CROSS-REFERENCE TO RELATED APPLICATIONS

The present application is a U. S. National Phase of International Application No. PCT/CA2019/051091 filed on Aug. 9, 2019 and claims benefit of U.S. Provisional Application No. 62/717,181 filed Aug. 10, 2018, the content of which is hereby incorporated by reference in its entirety.

TECHNICAL FIELD

It is provided an achiral, non-nucleosidic backbone for phosphoramidites and uses thereof in synthesis of nucleic acid strands and sequence-controlled oligo(phosphodiester)s.

BACKGROUND

Modified oligonucleotides such as DNA and RNA can be used in broad applications from gene silencing technologies to drug delivery, DNA nanotechnology, targeting therapies, nucleic acids biophysics studies, CRISPR/cas9 genome editing applications, dye labeled DNA and RNA for cellular, PCR primer functionalization and in vivo studies. Sequence-controlled polymers are essential tools in numerous fields such as molecular biology, drug design and therapy, medical imaging, materials science and nanotechnology. For these purposes, a strategy allowing the synthesis of monodisperse oligomers with a large number of chemical monomer variants is of great interest.

Novel methods, such as iterative exponential growth and other approaches have been introduced to make sequence controlled polymers in a scalable manner. However, solid-phase synthesis remains the method of choice for the most precise sequence control. Automated solid-phase phosphoramidite chemistry, in particular, has shown exceptional coupling yields for the synthesis of DNA and RNA. Decades of optimization have allowed it to attain the highest degrees of polymerization (DP) for a solid-phase synthesis. Up to 150 monomer-long oligonucleotides can be made in good yields and with simple purification methods. Importantly, the cost of phosphoramidite synthesis has been significantly and steadily declining, making it a practical as well as powerful strategy.

One of the most broadly available modifications is a serinol based modification as described in U.S. Pat. No. 8,394,948. Used several times on the same oligomer, this molecule will create mixtures of diastereoisomers that may be impossible to purify and may have different properties. This is particularly problematic for their use for biological applications where molecules of different chiralities can have vastly different activity (for example, one might be therapeutic and another chiral isomer may be toxic). The presence of diastereoisomers prevents the use of said serinol-based molecules for medical purposes since the FDA (Food and drug Administration) requires most molecules to be achiral or enantiomerically pure.

Solid-phase synthesis on a DNA synthesizer requires the phosphoramidite monomers to stay unaltered to a great number of chemical conditions (repetitive treatment with oxidant and mild acid and final deprotection in aqueous base). For the purpose of versatile and multiple functionalization of synthetic oligo(phosphodiester)s as encompassed herein, even more restricting conditions apply, making the task arduous. Due to a need for numerous monomers, their synthesis must be fast, cost effective and scalable. While phosphoramidite synthesis reports sometimes omit to specify attachment efficiency, very high coupling yields, leading to high DPs are essential. The monomer should preferably not contain a chiral center, or it must be enantiomerically pure. A mixture of enantiomers should be avoided as the stereochemical complexity of the oligomer increases exponentially with each monomer addition. Previous reports of non-nucleosidic phosphoramidites only partially satisfy these criteria. For example, propanediol (Nelson et al., 1992, Nucleic Acids Res., 20(23): 6253-6259), threoninol (Ito et al., 2010, Org. Biomol Chem., 8(24): 5519-5524) and serinol (U.S. Pat. No. 8,394,948) based phosphoramidites can be attached on a DNA strand but their synthesis starts either with racemic mixtures or costly enantiopure diols. Other reports show the elegant synthesis and use of hydroxyprolinol (Hébert et al., 1994, 35(51): 9509-9512) and oxamide (Kupryushkin and Pyshnyi, 2012, Russ. J. Bioorganic Chem., 38(6): 662-666) based phosphoramidites, but these may lead to stability issues during the final deprotection under basic conditions and their synthesis involves many steps.

Existing technologies either lead to racemic mixtures, less stable oligomers or the phosphoramidites are difficult or expensive to make.

There is thus still a need to be provided with a new molecule that can sequence-specifically modify oligonucleotides and sequence-controlled polymers in high yields without introducing two isomers each time it is added to the backbone. This molecule needs to be easy to make and prepared from readily available inexpensive chemicals.

SUMMARY

In accordance to an embodiment, it is provided a reagent having the following structure

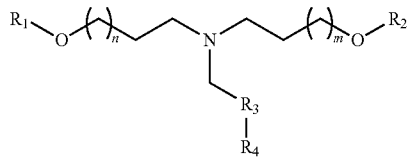

wherein:

R1 is dimethoxytrityl (DMT), monomethoxytrityl (MMT), or other hydroxyl protecting group stable to oligonucleotide synthesis conditions;

R2 is a phosphoramidityl residue

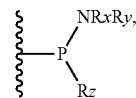

wherein Rx and Ry are independently selected from the group consisting of C1-10 branched alkyl, C1-12 alkyl, and cyclic hydrocarbyls; and Rz is a phosphite-protecting group; or R2 is H,
R3 and R4 together form an alkyl, ethynyl or propargyl residue; or
R3 is:
a homo or heteroarylene residue

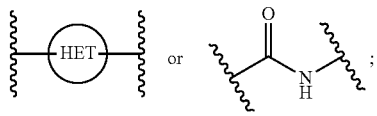

or R3 is an alkyl or oligo(ethylene glycol) chain with an amide or a heteroarylene residue on which is attached R4,
R4 is:
  an optionally protected amino-acid or short peptide covalently attached to said R3;
  a diaminoalkyl residue of general formula

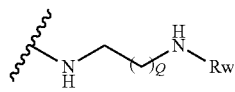

wherein Rw is an amino protecting group; or
an optionally protected monosaccharide residue covalently attached to R3;
a fluorophore, biotin, a strained alkyne, a disulfide, a protected thiol, a cross-linker or folic acid having suitable protecting groups,
n is an integer of 1 to 4,
m is an integer of 1 to 4, and
Q is an integer greater than 1.

In an embodiment, Rx and Ry are $CH(CH_3)_2$ and Rz is $O-(CH_2)_2-CN$.

In another embodiment, R1 is dimethoxytrityl (DMT).

In an additional embodiment, R3 is:

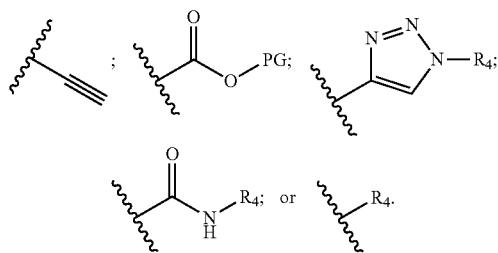

In a further embodiment, R4 is:

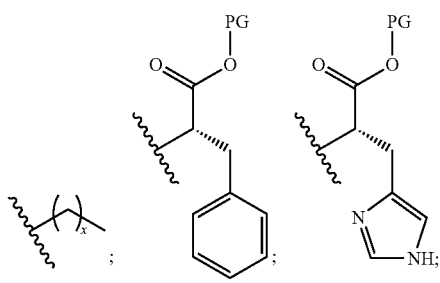

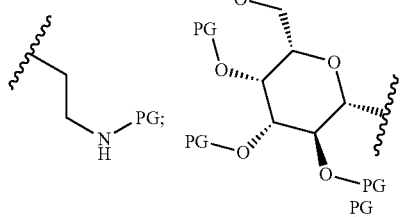

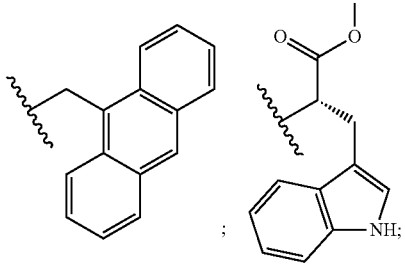

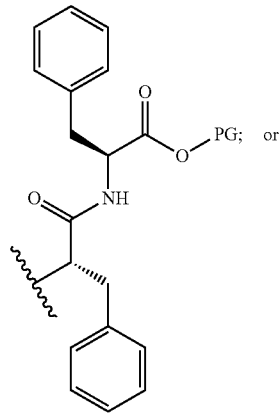

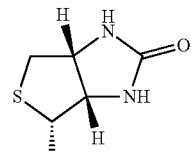

As encompassed herein, PG is a protecting group.

In an embodiment, the protecting group is an ester group or an acetate group.

In another embodiment, the protecting group is, a silylated group, a trifluoroacetate group, a fluorenylmethyloxycarbonyl (FMOC) group, a monomethoxytrityl group, a 4-tertbutylbenzoyl group, a trityl group, an isobutyrate group, a trifluoroacetic acid (TFA) group or a methyl ester group.

In another embodiment, the reagent described herein further comprises an amine functionalized with a carboxylic acid.

In an embodiment, the amine is functionalized with an amino acid, a carbohydrate, a short peptide, a fluorophore, biotin, a strained alkyne, a disulfide, a protected thiol, a cross-linker or folic acid having suitable protecting groups.

In a particular embodiment, the reagent described herein comprises the following structures:

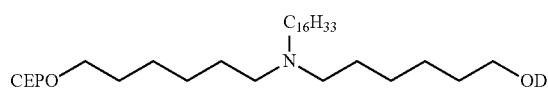

1

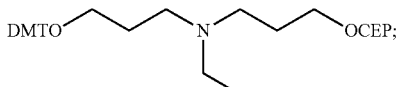

2

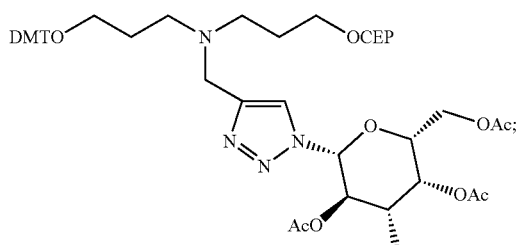

3

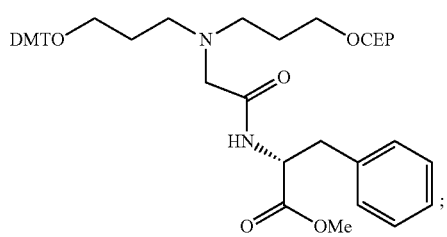

4

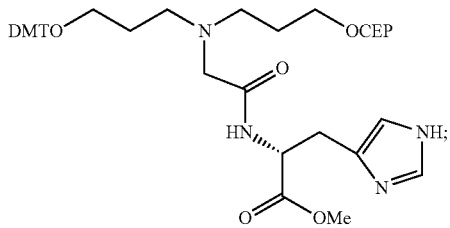

5

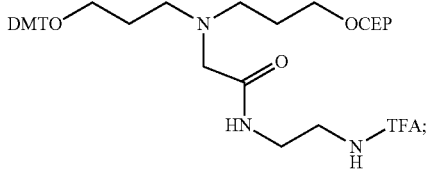

6

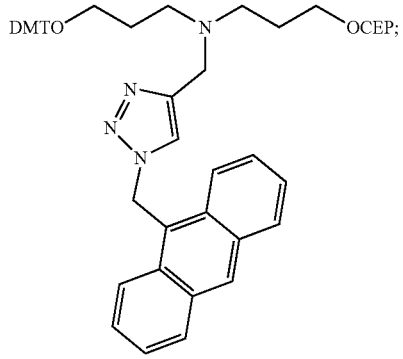

7

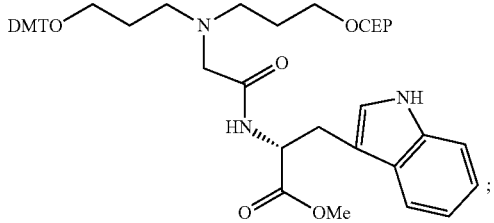

8

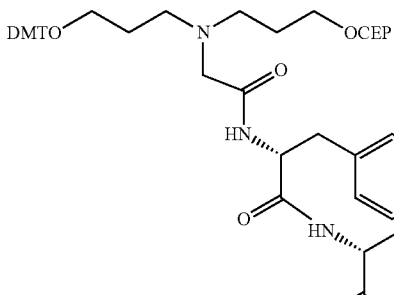

9; or

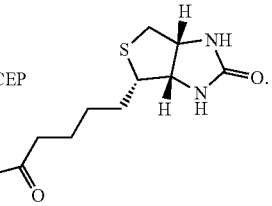

10

It is further provided a process to modify a synthetic oligonucleotide and/or to make a sequence-controlled oligomer, at any positions wherein the process comprises covalently attaching the reagent as defined herein, into said oligonucleotide and/or sequence-controlled oligomer by performing a phosphoramidite coupling during a synthesis of said oligonucleotide and/or sequence-controlled oligomer.

In an embodiment, the oligonucleotide and/or sequence-controlled oligomer is functionalized with a fluorophore, biotin, a strained alkyne, a disulfide, a protected thiol, a cross-linker or folic acid having suitable protecting groups.

In another embodiment, the process described herein further comprises the possibility of functionalizing the oligonucleotide and/or sequence-controlled oligomer after the phosphoramidite couplings using click chemistry.

In another embodiment, the fluorophore is a Cy5 sulfonated dye.

In a further embodiment, the synthetic oligonucleotide and/or sequence-controlled oligomer is modified or made in an automated synthesizer.

BRIEF DESCRIPTION OF THE DRAWINGS

Reference will now be made to the accompanying drawings.

DETAILED DESCRIPTION

It is provided an achiral, non-nucleosidic backbone for phosphoramidites that can be inserted with high yields in nucleic acid strands and sequence-controlled oligo(phosphodiester)s through solid phase synthesis (SPS) using a DNA synthesizer. Yields are high enough (>90%) to consider multiple introductions of different functionalities. From this backbone, two platforms with useful chemical handles were developed and attached to nucleic acid strands and sequence-controlled oligo(phosphodiester)s (2P, 11P). In addition, these platforms are customizable with a large variety of chemical functionalities or molecules of interest before SPS in two high yielding steps from platforms 2' and 11', giving access to a whole library of novel achiral phosphoramidites presenting biological, biophysical or chemical interest. In general, all phosphoramidites having this design are made in few steps and with low costs compared to existing technologies. Post-SPS modifications are possible.

Figure 3:
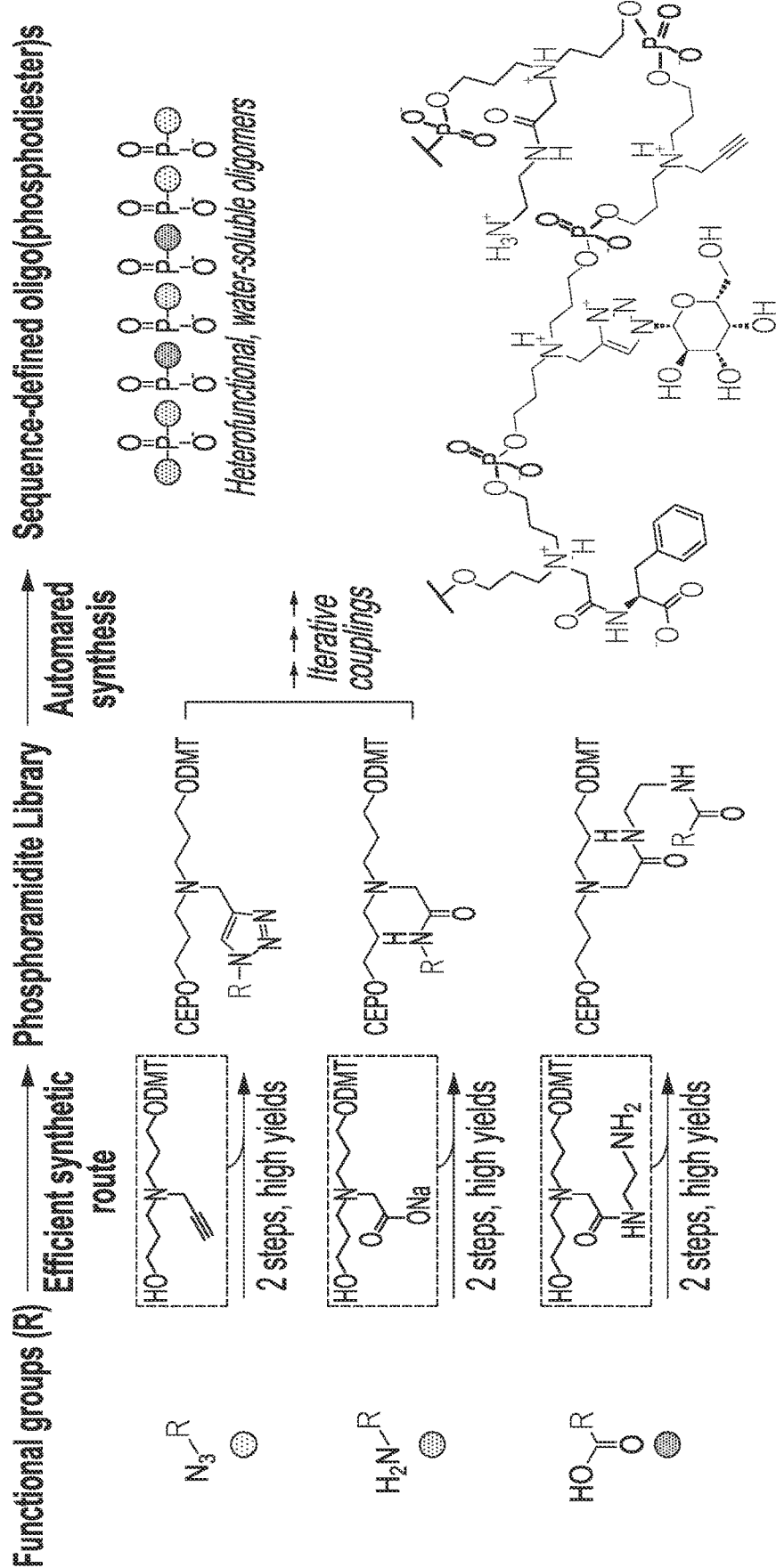
FIG. 3 illustrates the synthesis of sequence-controlled oligo(phosphodiester)s made of monomers based on the novel tertiary amine backbone in accordance with an embodiment, wherein the four moieties shown on the oligo (phosphodiester) (phenylalanine (4), β-D-glucose (3), alkyne (2) and amino (6)) are used as examples of what could be made.

The alkyne-containing unit 2' would allow the introduction of azides such as sugar molecules, while the carboxylate-containing molecule 11' would allow functionalization with amine containing monomers, including amino acids such as phenylalanine and histidine (see FIG. 3). Applicability of this strategy was tested with the synthesis of a variety of modified DNA strands and fully artificial oligo (phosphodiester)s. Accordingly, it is provided a tertiary amine backbone used as a cost-effective and more efficient alternative to commercially available DNA modifications.

There is a 3-carbon spacer between the central nitrogen and the two external hydroxyls of the platforms 2' and 11' and reagents 1-6. This is an optimized spacer, as a 2-carbon spacer results in poorer coupling yields and instability, due to the formation of an intramolecular 5-membered ring that can cleave the backbone (de Rochambeau, et al, Polymer Chem. 2016). Molecule 1 has a six-carbon spacer which results in good coupling yields as well.

The strategy described herein makes oligonucleotides and sequence-defined polymers based on automated phosphoramidite solid-phase synthesis (Edwardson et al., 2014, Angew. Chem. Int. Ed. Engl., 53: 4567-4571). This method allows the formation of poly(phosphodiester)s that are highly soluble in water due to their anionic nature, very stable and biodegradable thanks to their phosphodiester linkage.

Figure 4:
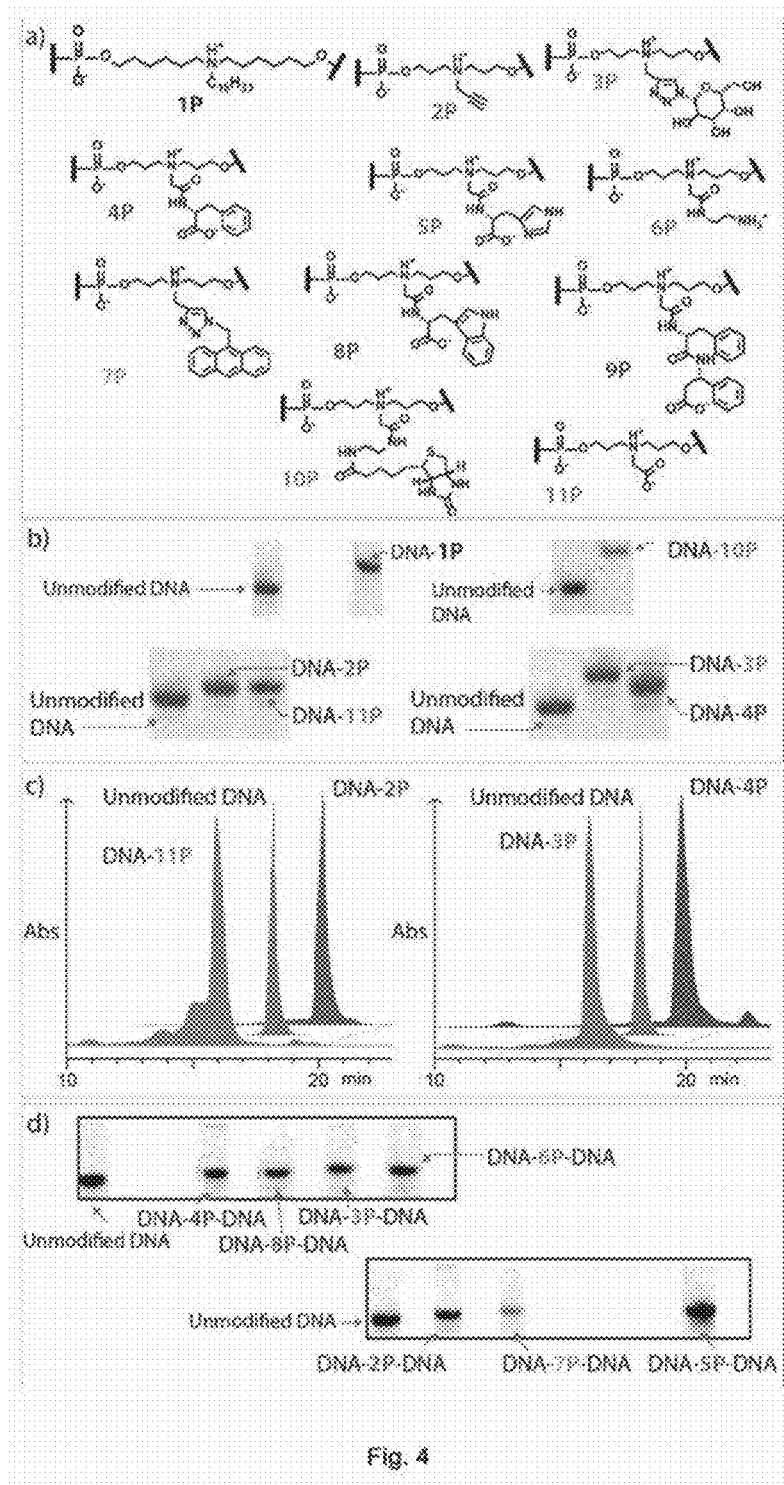
FIG. 4 illustrates (a) the chemical formulas of the versions of 1-10 and 11' (named 1P-11P) after automated synthesis and deprotection; (b) the electrophoretic mobility gel assay for DNA 19mers modified with 1-5, 10-11 at the 5'-end; (c) the reverse-phase (RP) HPLC traces (UV detection, 260 nm) from crude mixtures, wherein DNA sequence is: 5'-TTTTTCAGTTGACCATATA-3' (SEQ ID NO: 1); (d) the electrophoretic mobility gel assay for DNA 19mers modified with 2-8 internally (shown with an X in the sequence), wherein DNA sequence is: 5'-TA-X-TTTTTCAGTTGAC-CATATA-3' (SEQ ID NO: 2).
Figure 5:
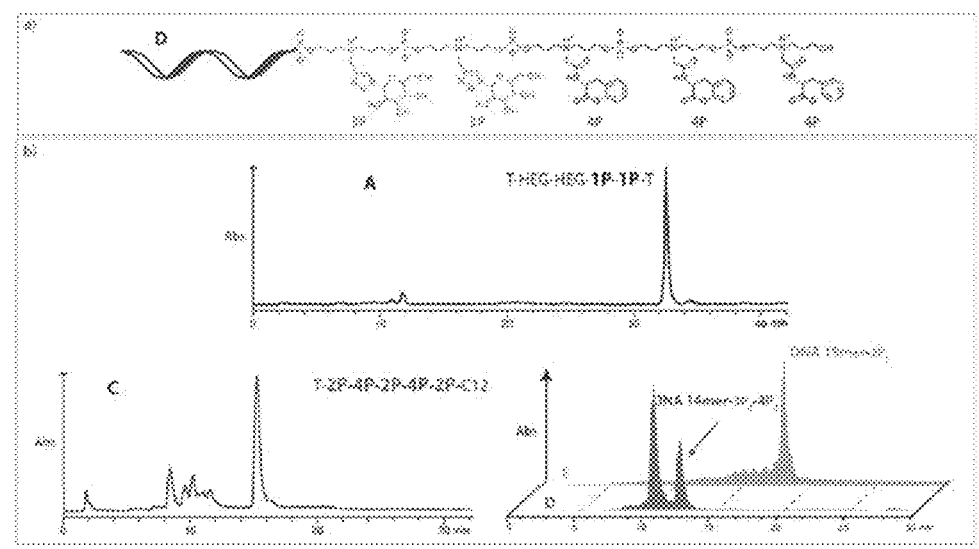
FIG. 5 illustrates (a) the formula of DNA oligomer D (b) representative reverse-phase (RP) HPLC traces (UV detection, 260 nm) from crude mixtures of sequence-controlled oligo(phosphodiester)s A, C, D and E, wherein all main peaks were found to be the expected product (except for DNA oligomer D for which the second peak is associated to the product), T stands for thymidine, HEG for a commercially available hexaethyleneglycol monomer, C12 is a commercially available 12 carbons long alkyl chain monomer. DNA-19mer sequence is 5'-TTTTTCAGTTGAC-CATATA-3'. DNA-14mer sequence is 5'-CAGTTGAC-CATATA-3' (SEQ ID NO: 3).

To make molecule 1, bromohexanol was substituted onto hexadecylamine, leading to compound 1' further transformed to 1. This molecule was successfully attached to a DNA 19 mer (yields of 90-96%) and on a sequence-controlled oligo(phosphodiester) (FIGS. 4-5). It shows that the tertiary amine backbone with 6 carbons between the DMT or CEP and the central nitrogen is also adapted.

Figure 1:
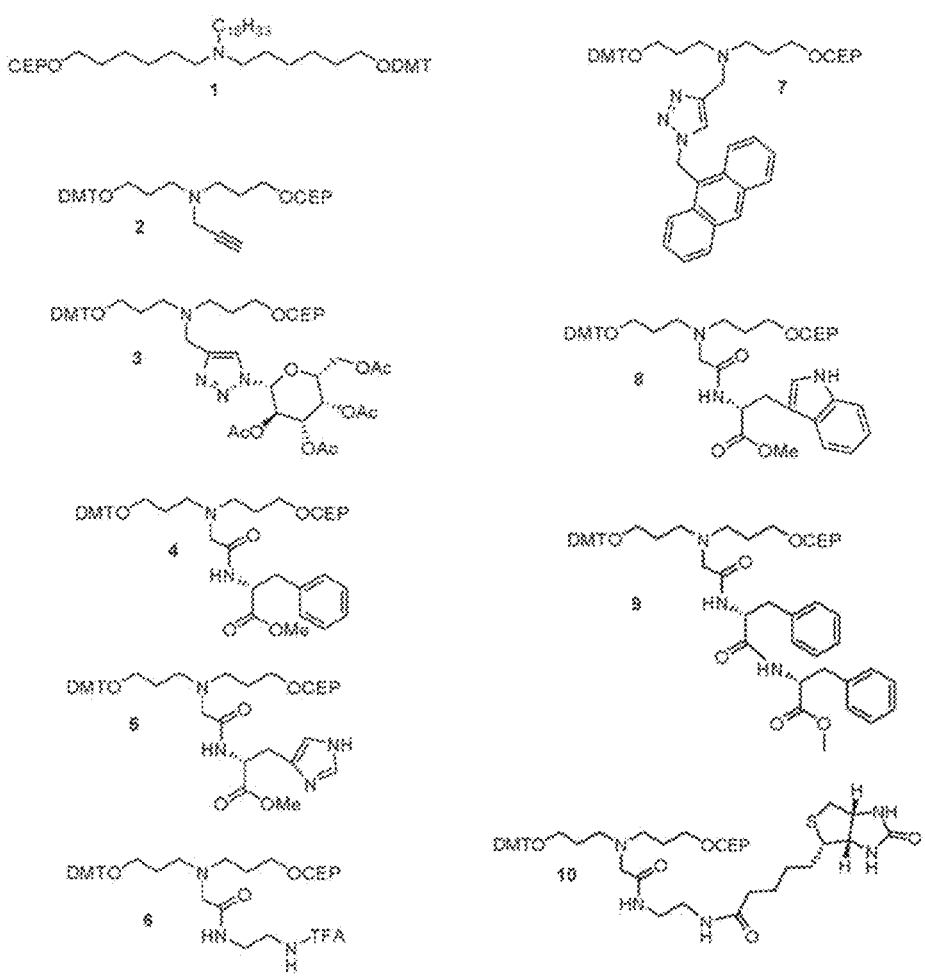
FIG. 1 illustrates embodiments wherein the tertiary amine structure is connected to alkyl chain (1), an alkyne (2), a carbohydrate (3), three amino acids (4,5,8), an amino group (6), a fluorophore that may be used as a cross-linker (7), a dipeptide (9), biotin (10).
Figure 2:
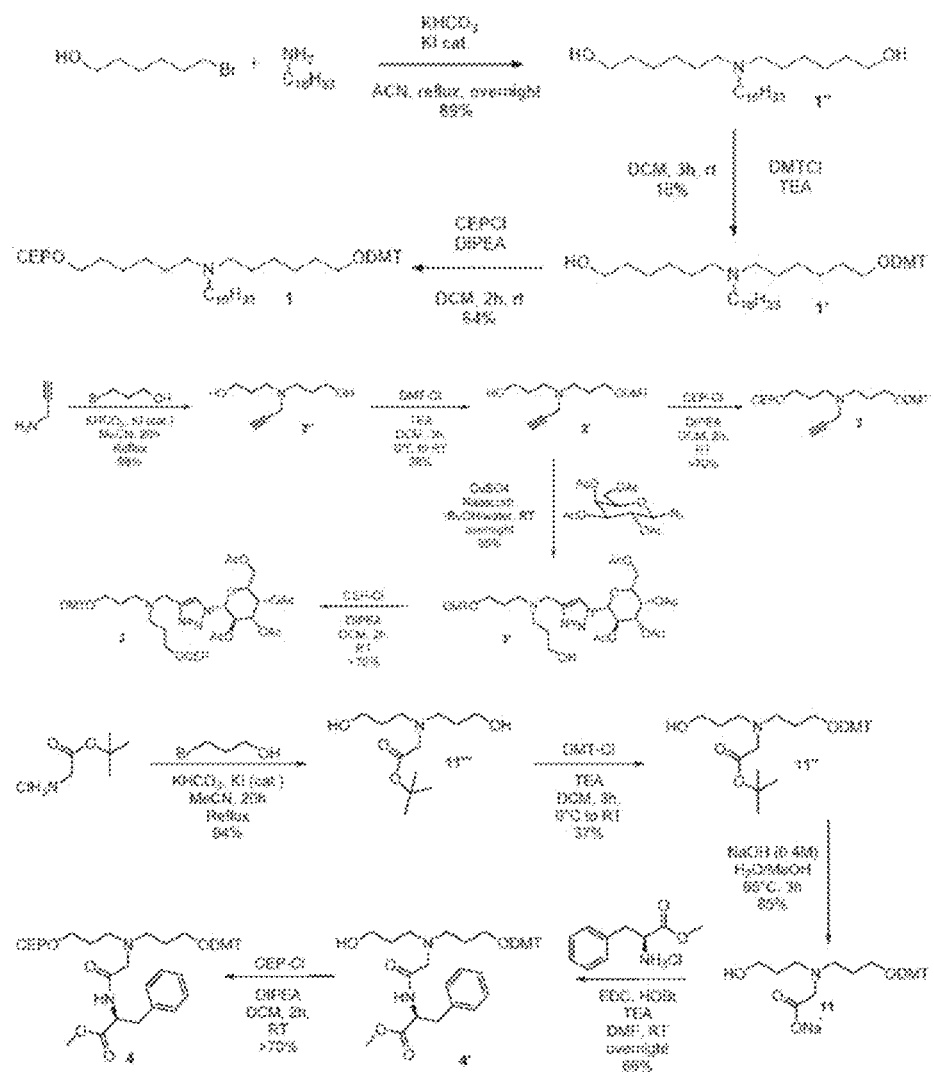
FIG. 2 shows the synthetic route for molecules 1-10.
Figure 2:
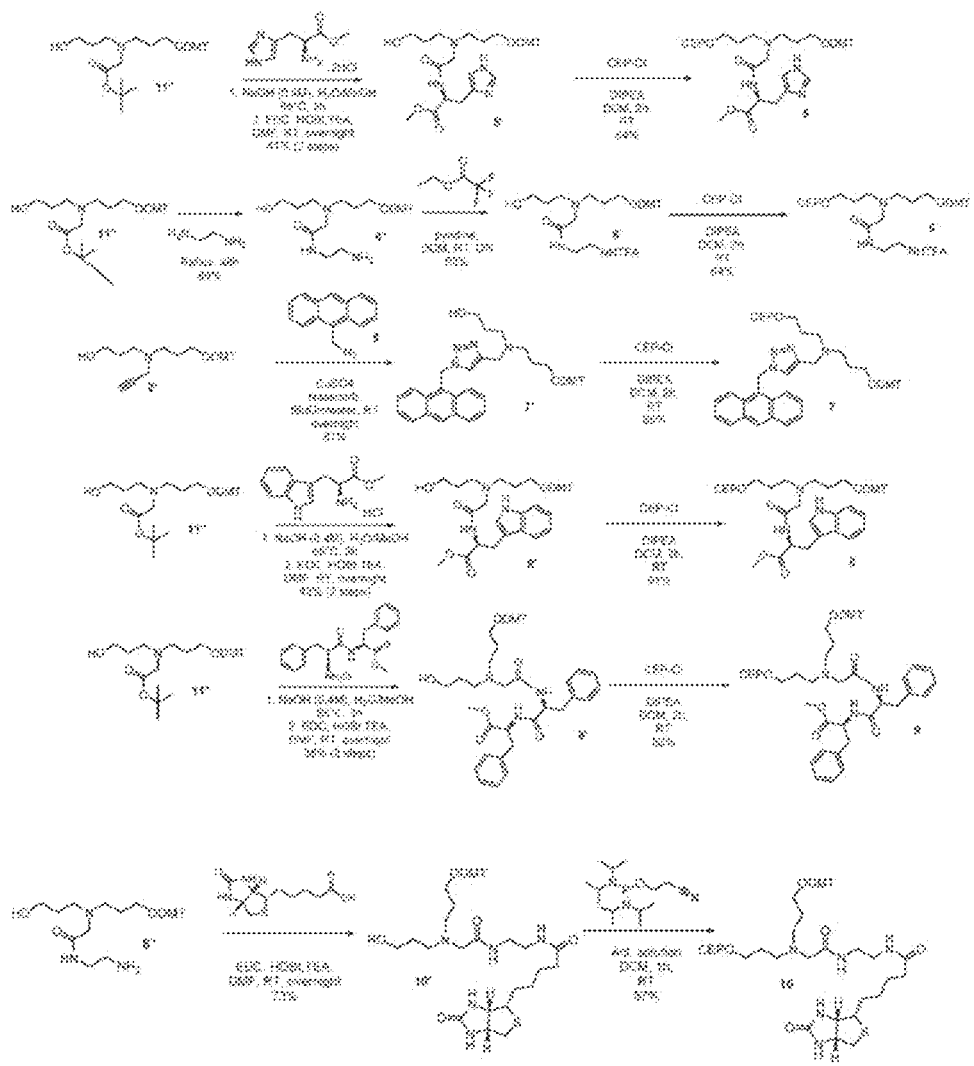

Two molecules were synthesized to be used as versatile platforms to attach a variety of moieties. Molecules 2' and 11' have many advantages: they are easy to synthesize in two steps for 2' and three for 11' from readily available, inexpensive starting materials, they need only one chromatography purification and they have a reactive function for simple and efficient attachment of the moiety of interest. Furthermore, the DMT monoprotection being the lowest yielding step, the material waste can be limited by performing it as the second step and attach the moiety of interest afterwards. Compound 2' has an alkyne moiety for click chemistry. Many bio-related compounds are now available as azides making this platform highly versatile for possible functionalization with carbohydrates, dyes, biotin-bearing or cyclodextrin containing molecules for example. Oligomers from 2' can possibly have zwitterionic character, due to protonation of their tertiary amine moiety. Compound 11' is of interest as well since its carboxylate allows common amide coupling with readily available amines such as amino acids or peptides. These two platforms were synthesized with good yields after double alkylation of propargylamine and glycine t-butyl ester (FIG. 2) respectively with bromopropanol, followed by DMT protection of one hydroxyl group. 2' and 11" were attached to a DNA strand without isolation of the phosphoramidite using standard solid-phase synthesis. Final oligomer deprotection procedure from the solid support led to modified DNA strands. Modifications after deprotection are called 1P-11P (FIG. 4) in reference to the phosphodiester linkage formed between the new monomer and DNA. Good coupling yields confirmed that 2' and 11' backbones are suitable for phosphoramidite-based SPS (FIG. 4, Table 1).

TABLE 1

Yields and ESI-MS characterization of modified 19mers containing 2P, 7P.

| Modification | Incorporation yields[a] (%) | Calculated exact mass [g mol$^{-1}$] | Found exact mass[c] [g mol$^{-1}$] |
|---|---|---|---|
| 2P | 93-99 | 5998.06 | 5998.00 |
| 11P | 90-92 | 6018.05 | 6018.01 |

[a]Yields were calculated through image analysis of electrophoretic mobility shift assays and through product peak area by RP-HPLC (260 nm detection) vs unmodified DNA.
b: Product peak area by RP-HPLC over total UV absorption during the run.
[c]Mass was found using ESI-MS technique, detecting multiply charged species.

2' was also turned into phosphoramidite 2 and introduced many times on a DNA strand and on sequence-controlled oligo(phosphodiester)s (FIG. 5, Table 3).

In addition, 2' and 11' were functionalized with model molecules. A protected sugar azide was chosen, as well as a methyl ester amino acids, phenylalanine and histidine. Standard click chemistry procedure was performed to obtain molecule 3' in 95% yields and molecule 7' in 87% yields which were then turned into phosphoramidites 3 and 7. Molecule 7 is a fluorophore and can be used as a cross-linking reagent. Indeed, it is susceptible to form dimers upon irradiation with UV light. Only one chromatography purification is required to make 3 or 7 from 2'. Phenylalanine, histidine, tryptophan and L-Phenylalanyl-L-phenylalanine methyl esters could be coupled successfully to 11' and the obtained molecules were turned into monomers 4, 5, 8 and 9. 5 is interesting as a ligand for a metal like zinc for example while tryptophan has been showing to enhance the binding affinity of aptamers (Rohloff et al., Mol. Ther. Nucleic Acids, 2014, 3, e201) and 9 may be used for self-assembly purposes. Successful incorporation of 3, 4, 5 and 8 on a DNA strand was achieved and high incorporation yields were obtained (FIG. 4, Table 2). 9 was also shown to be successfully incorporated at the 5' end of a DNA 19mer (calculated molecular weight: 6312.20; found: 6312.19). The deprotection conditions used are suitable for classic DNA synthesis. As a conclusion, it is shown the simple and cost-effective incorporation of an azide molecule or a primary amine bearing compound in DNA strands. Due to the non-chiral character of the platforms used and the good to excellent incorporation yields obtained, these molecules are thus good candidates for the efficient preparation of sequence controlled oligomers with a variety of side chain functions. Finally, the ease of preparation of 2', 11' and their functionalized counterparts illustrates the great practicality and ready accessibility of the phosphoramidites described herein.

TABLE 2

Yields and ESI-MS characterization of modified 19mers containing monomers 3-8, 10.

| Modification | Incorporation yields[a] (%) | Calculated exact mass [g mol$^{-1}$] | Found exact mass[b] [g mol$^{-1}$] |
|---|---|---|---|
| 3 | 91 | 6203.13 | 6203.13 |
| 4 | 92 | 6165.13 | 6165.01 |
| 5 | 91 | 6154.94 | 6155.12 |
| 6 | 89 | 6031.16 | 6031.09 |
| 7 | 92 | 6231.17 | 6231.25 |
| 8 | 90 | 6204.14 | 6204.25 |
| 10 | 99 | 6286.20 | 6286.16 |

[a]Yields were calculated through image analysis of electrophoretic mobility shift assays vs unmodified DNA.
[b]Mass was found using ESI-MS technique, detecting multiply charged species.

For the incorporation of compounds 4, 5, 8 and 9 deprotection of the oligomers using t-butylamine/water (1:3) for 6 hours at 65° C., sometimes followed by a deprotection in concentrated ammonium hydroxide solution overnight at 65° C., allowed the quantitative conversion of the methyl ester on the amino acid into the carboxylate derivative (4P and 5P), while fast deprotection using standard methylamine/ammonium hydroxide conditions allowed the quantitative conversion of the methyl ester on the amino acid into the secondary methyl amide derivative.

As described herein, an amine bearing molecule (6"), made in one step from 11", was shown to be used as a chemical handle for further functionalization with carboxylic acids (dyes, biotin, disulfide, protected thiols, etc) before SPS. This has been exemplified with the synthesis of phosphoramidite 10 in two steps from 6" functionalized with biotin and successfully incorporated in oligonucleotides in high yields (see FIG. 4, Table 2) It can also be considered for post SPS modifications once it has been protected with a trifluoroacetate group that is removed during final oligomer deprotection. Yields of attachment of phosphoramidite 6 to a DNA 19mer have been found to exceed 90%.

Other examples of oligonucleotides modified with monomers 2-8 at internal positions revealed very high coupling yields (FIG. 4, Table 3).

TABLE 3

Yields and ESI-MS characterization of modified 21mers containing monomers 2-8 between the $2^{nd}$ and the $3^{rd}$ nucleotide (from 5' to 3').

| Modification | Incorporation yields[a] (%) |
|---|---|
| 2 | 95 |
| 3 | 95 |
| 4 | 97 |
| 5 | 91 |
| 6 | 95 |
| 7 | 95 |
| 8 | 94 |

[a]Yields were calculated through image analysis of electrophoretic mobility shift assays vs unmodified DNA.

The new tertiary amine platforms allowed the modular and highly efficient synthesis of sequence-controlled oligomers featuring different moieties. The phosphoramidites were used in a standard automated DNA synthesizer along with commercially available DNA synthesis reagents. Coupling cycles were the same than for DNA synthesis except that the coupling time was increased to 10 minutes and phosphoramidite concentration was kept about 0.1 M in dichloromethane. After synthesis and deprotection, isolation could be performed using RP-HPLC and the oligomers were further characterized using LC-MS techniques. Thanks to the ionic nature of the polymers described herein, they are perfectly soluble in water leading to great ease of manipulation. They can be quantified easily using the absorbance coefficients of nucleobases at 260 nm. Yields were measured on the HPLC traces considering the relative absorbance of each byproduct. Most sequences were designed to show high functional diversity on one chain. New monomers based on the tertiary amine backbone were used (1, 2, 3, 4), combined with commercially available monomers (nucleotides and hexaethyleneglycol, HEG) and a commercially available hydrophobic 12 carbon long chain phosphoramidite (C12). Except in one case, all coupling yields were found to be over 90% (Table 4, FIG. 5).

TABLE 4

Yields and ESI-MS characterization of sequence-controlled oligo(phosphodiester)s.

| Oligomer | Sequence (iterative synthesis from left monomer) | Global yields[a] (%) | Average individual coupling yields[b] (%) | Calculated exact mass [g mol$^{-1}$] | Found exact mass[c] [g mol$^{-1}$] |
|---|---|---|---|---|---|
| A | T-HEG-HEG-1-1-T | 82 | 97 | 2241.20 | 2241.03 |
| B | T$_3$-HEG$_4$-3-2$_2$ | 60 | 93 | 3130.99 | 3130.97 |
| C | T-2-4-2-4-2-C12 | 52 | 90 | 2005.76 | 2005.74 |
| D | DNA 14mer-3$_2$-4$_3$ | 34 | 81 | 6321.47 | 6321.44 |
| E | DNA 19mer-2$_5$ | 82 | 96 | 6930.39 | 6930.16 |

[a]Yields were calculated through product peak area by RP-HPLC (260 nm detection) considering the relative absorbance (SI-V) of byproducts.
[b]These numbers were obtained by taking the global yields at the power 1/n, n being the number of couplings after the closest nucleotide.
[c]Mass was found using ESI-MS technique, detecting multiply charged species.

Interestingly, DNA strands containing several glycosyl modifications are provided herein as well as amino acids (oligomer D). Indeed, a DNA 14mer was functionalized twice with phosphoramidite 3 followed by three times with 4. To functionalize an oligomer with a large number of the same azide modification, post-SPS functionalization can be considered. Indeed, two DNA 19mers were synthesized containing respectively 1 (FIG. 5) and 5 alkyne moieties (96% individual coupling yields, oligomer E). Following a straightforward protocol for copper catalyzed cycloaddition on oligonucleotides, high yielding functionalization of these strands with β-D-glycosyl azide was achieved (>80%). Functional diversity imparted by the strategy disclosed here in DNA strands could significantly expand the toolbox of DNA nanotechnology.

The new tertiary amine backbone may be protonated at pHs under 10. Therefore, the sequence-controlled oligomers formed are to be more soluble in water than the other non-nucleosidic phosphoramidites reported.

Accordingly, it is described a strategy to make a variety of phosphoramidite monomers that can be used in an automated synthesizer for the synthesis of sequence-controlled oligomers and modification of nucleic acids. Several achiral tertiary amine backbones were tested to be used as platforms for making a large variety of phosphoramidite monomers. This led to the design of several phosphoramidites that could be obtained in a few simple synthetic steps from inexpensive starting materials. Their attachment on DNA strands was shown to be very efficient.

Since the positive charge of Cy5 has been shown to greatly influence cellular uptake of drug delivery devices (Lorenz et al., 2011, Microscopy and Microanalysis, 17(3): 440-445), the use of negatively charged (e.g. sulfonated) dyes can be of interest. It is shown the possibility of doing a post SPS functionalization of 96mers with a Cy5 sulfonated dye at two different positions (one example at position 25 and one example at position 97, Table 5). The DNA strand is first modified with the alkyne phosphoramidite as described herein and further functionalized post-SPS using click chemistry. Strands were isolated by gel electrophoresis purification followed by HPLC purification. MS characterization confirmed the right attachment of the sulfonated dye to 2P. Modification of strands of this size is not trivial so these results further exemplify the utility of the alkyne phosphoramidite described herein.

TABLE 5

ESI-MS characterization of long sequences modified with a sulfonated dye.

| Position modified with 2 | Calculated molecular weight [g mol$^{-1}$] | Found molecular weight[a] [g mol$^{-1}$] |
|---|---|---|
| 25 | 30,524 | 30,585 |
| 97 | 30,524 | 30,604 |

[a]Mass was found using ESI-MS technique, detecting multiply charged species.

Sequence used: 5'-CCACACTTGCTTTTTCCTATATGGT-CAACTGCTCTTTTCTGACCAGTGTCAGCAAACCTTTTGTAGTAATACCAGATGGAGTTTTTGTGTGCGTGC-3' (SEQ ID NO: 4)

Example I

General Information and Instrumentation

All starting materials were obtained from commercial suppliers and used without further purification unless otherwise noted. Dimethoxytrityl chloride (DMT-Cl) was purchased from GenScript. (3-Dimethylaminopropyl)-N'-ethyl-carbodiimide hydrochloride (EDC-Cl), glycine tert-butyl ester hydrochloride were purchased from AKScientific. 3-bromo propanol was purchased from Alfa Aesar. Acetic acid, Boric acid, solvents were purchased from Fisher Scientific. Chloroform-d1 was purchased from Cambridge Isotope Laboratories. Importantly, it was stored on molecular sieves in order to keep it neutral. If used as sold, hydrolysis of phosphoramidite (fast) as well as DMT deprotection (slow) may be observed. GelRed™ nucleic acid stain was purchased from Biotium Inc. Concentrated ammonium hydroxide, ammonium persulfate, acrylamide/Bis-acrylamide (40% 19:1 solution) and TEMED were obtained from Bioshop Canada Inc. and used as supplied. 1 µmol Universal 1000 Å LCAA-CPG supports and standard reagents used for automated DNA and RNA synthesis were purchased through Bioautomation. N,N-diisopropylamino Cyanoethyl phosphonamidic-chloride (CEP-Cl) and DMT-hexaethyloxy glycol (cat. #CLP-9765) phosphoramidites were purchased from Chemgenes. Sephadex G-25 (super fine, DNA grade) was purchased from Glen Research. All other reagents were obtained from Sigma-Aldrich. TEAA (triethylammonium acetate) buffer is composed of 50 mM TEA with pH adjusted to 8.0 using glacial acetic acid. TBE buffer is 90 mM Tris, 90 mM boric acid and 1.1 mM EDTA with a pH of 8.0.

Standard automated solid-phase synthesis was performed on a Mermade MM6 synthesizer from Bioautomation. HPLC purification was carried out on an Agilent Infinity 1260. DNA and oligomers quantification measurements were performed by UV absorbance with a NanoDrop Lite spectrophotometer from Thermo Scientific. A Varian Cary 300 Bio spectrophotometer was used for UV absorbance studies. Polyacrylamide Gel Electrophoresis (PAGE) experiments were carried out on a 20×20 cm vertical Hoefer 600 electrophoresis unit. Gel images were captured using a ChemiDoc™ MP System from Bio-Rad Laboratories. Dry solvents were taken from an Innovation Technology device. Low Resolution Mass determination was carried out using Electron-Spray Ionization-Ion Trap-Mass Spectrometry (MS) on a Finnigan LCQ Duo device. High Resolution mass determination was achieved using a Bruker Maxis API (Atmospheric pressure ionization) QTOF or a THERMO Exactive Plus Orbitrap-API. Liquid Chromatography Electrospray Ionization Mass Spectrometry (LC-ESI-MS) of oligomers was carried out using Dionex Ultimate 3000 coupled to a Bruker MaXis Impact™ QTOF. Some oxygen and moisture sensitive experiments were carried out in a Vacuum Atmospheres Co. glove box. Column chromatography was performed using a CombiFlash Rf system from Teledyne Isco. The NMR spectra were recorded on Bruker 400 MHz, 500 MHz, Varian 300 MHz or 400 MHz for 1H, 13C and 31P with chloroform-d1 ($\delta$ 7.26, 1H; $\delta$ 77.16, 13C), acetone-d6 ($\delta$ 2.04, 1H; $\delta$ 29.8, 13C) or DMSO-d6 ($\delta$ 2.50, 1H; $\delta$ 39.5, 13C) as internal lock solvents and chemical shift standard.

General Procedure for Dimethoxytrityl Protection 3.63 mmol of the diol starting material and 1.47 ml of TEA (10.9 mmol, 3 equiv.) were dissolved in 30 ml of dry dichloromethane (DCM) in a 100 ml dry round bottom flask. DMT chloride (1.23 g, 3.63 mmol, 1 equiv.) was dissolved in 20 ml of dry DCM and added drop wise to the reaction mixture at 0° C. under vigorous stirring. After the chloride addition, the reaction was allowed to warm up to room temperature and left under stirring for 2 h 30 min.

General Procedure for Converting the Monoprotected Alcohols into Phosphoramidites (Except Molecule 10)

Monoprotected diol was suspended in toluene or acetonitrile and solvent was evaporated under reduced pressure (60° C.). The operation was repeated once and the dried compound was kept under high vacuum for at least 5 hours. In an oven-dried flask, 0.64 mmol of alcohol starting material were then dissolved in anhydrous DCM (5 ml) and 0.56 ml of dry DIPEA (3.2 mmol, 5 equiv.) was added under stirring. CEP-Cl (0.14 ml, 0.64 mmol, 1 equiv.) was added slowly and the reaction was allowed to stir under inert gas at room temperature for 2 hours. Two fast extractions with DCM from a 10% $Na_2CO_3$ aqueous solution were performed. Organic fractions were combined, dried over $MgSO_4$, filtered and the solvent was evaporated under reduced pressure (40° C.). The crude product was loaded on celite and purified using the combiFlash system.

6,6'-(hexadecylazanediyl)bis(hexan-1-ol), (1''). To a solution of hexadecylamine (121 mg, 0.5 mmol) in acetonitrile were added $KHCO_3$ (200 mg, 2 mmol, 3 equiv.), KI (17 mg, 0.1 mmol, 0.2 equiv.) and 6-bromo-1-hexanol (0.131 ml, 1.0 mmol, 2 equiv.) under stirring. Temperature was raised until a reflux of acetonitrile was reached and left under stirring overnight. The reaction was followed by TLC. After completion, the reaction was worked up with saturated $NaHCO_3$ solution and DCM. The organic layer was collected, dried over $MgSO_4$, filtered and solvent was evaporated under reduced pressure (40° C.). 197 mg of a yellow oil were obtained (89%). Compound obtained was found to be pure up to 90% (NMR) and was used as is for the next step. $^1$H NMR (500 MHz, $CDCl_3$): $\delta$ (ppm) 3.67 (m, 4H), 2.40 (m, 5H), 1.63-1.23 (m, 45H), 0.91 (t, J=5 Hz, 3H).

6-((6-(bis(4-methoxyphenyl)(phenyl)methoxy)hexyl) (hexadecyl)amino)hexan-1-ol, (1'). Reaction was performed from 1.54 mmol of 1''. Product was extracted twice with DCM from a 10% $Na_2CO_3$ aqueous solution, washed once with a 10% $Na_2CO_3$ aqueous solution, dried over $MgSO_4$, filtered and solvent was evaporated under reduced pressure (40° C.). The crude product was loaded on celite and purified using the combiFlash system with a 4 g $SiO_2$ Gold column. Hexanes/TEA (10:1) and ethyl acetate were used in a gradient from 0 to 50% EtOAc. A clear yellow oil was isolated (204 mg, 18%). LRMS: Calc. exact mass: 743.6 g/mol. Measured (positive mode): 744.4 (M+1), 303.3 (DMT$^+$). $^1$H NMR (400 MHz, $CDCl_3$): $\delta$ (ppm) 7.45 (d, J=7 Hz, 2H), 7.35-7.29 (m, 6H), 7.23 (t, J=7 Hz, 1H), 6.85 (d, J=9 Hz, 4H), 3.65 (t, J=4 Hz, 2H), 3.05 (t, J=4 Hz, 2H), 2.43-2.35 (m, 6H), 1.67-1.55 (m, 7H), 1.49-1.22 (m, 41H), 0.91 (t, J=4 Hz, 3H).

6-((6-(bis(4-methoxyphenyl)(phenyl)methoxy)hexyl) (hexadecyl)amino)hexyl (2-cyanoethyl) diisopropylphosphoramidite, (1). Reaction was performed from 0.20 mmol of 1'. Purification was achieved with a 12 g $SiO_2$ "Gold" column. The solvents used were hexanes/TEA (10:1) and ethyl acetate in a gradient from 0 to 10% EtOAc in ~10 CV. A clear transparent oil was isolated (121 mg, 64%). HRMS (ESI-QTOF) m/z: [M+H]$^+$ Calcd for $C_{58}H_{95}O_5N_3P$ 944.7004; Found 944.6990. $^1$H NMR (500 MHz, $CDCl_3$): $\delta$ (ppm)=7.43-7.44 (m, 2H), 7.33-7.26 (m, 6H), 7.21-7.8 (m, 1H), 6.82 (d, J=9 Hz, 4H), 3.87-3.76 (m, 8H), 3.69-3.54 (m, 4H), 3.03 (t, J=7 Hz, 2H), 2.62 (t, J=7 Hz, 2H), 2.39-2.35 (m, 6H), 1.61 (quin., J=7 Hz, 2H), 1.45-1.34 (m, 10H), 1.31-1.22 (m, 32H), 1.18 (t, J=6 Hz, 12H), 0.88 (t, J=7 Hz, 3H). $^{13}$C NMR (126 MHz, CDCl$_3$): δ (ppm)=158.4, 145.6, 136.9, 130.1, 128.3, 127.8, 126.6, 117.8, 113.0, 85.7, 63.9, 63.7, 63.6, 58.5, 58.3, 55.3, 54.4, 54.3, 54.3, 43.1, 43.0, 32.0, 31.4, 30.3, 29.8, 29.8, 29.5, 27.8, 27.7, 27.5, 27.2, 27.1, 26.5, 26.1, 24.8, 24.7, 24.7, 24.7, 22.8, 20.5, 20.4, 14.2. $^{31}$P NMR (203 MHz, CDCl$_3$): δ (ppm)=147.3.

3,3'-(prop-2-yn-1-ylazanediyl)bis(propan-1-ol), 2". To a solution of propargylamine (551 mg, 10.0 mmol) in acetonitrile were added KHCO$_3$ (3.00 g, 30.0 mmol, 3 equiv.), KI (166 mg, 1 mmol, 0.1 equiv.) and 3-bromo-1-propanol (1.82 ml, 20.00 mmol, 2 equiv.) under stirring. Temperature was raised until a reflux of acetonitrile was reached and left under stirring overnight. The reaction was followed by TLC. After completion, solid was filtered out and solvent was evaporated under reduced pressure (40° C.). Crude obtained was resuspended in DCM, filtered, dried over MgSO$_4$, filtered and solvent was evaporated under reduced pressure (40° C.). 1.68 g of a dark brown red oil were obtained. (98%). Compound obtained was found to be pure up to 90% (NMR) and was used as is for the next step. NB: in order to get good characterization data, some compound could be further purified using the CombiFlash with a SiO$_2$ Gold column, (80:20:2 DCM:EtOH:NH$_4$OH). $^1$H NMR (500 MHz, CDCl$_3$): δ (ppm) 3.76 (t, J=6 Hz, 4H), 3.50 (d, J=2 Hz, 2H), 2.76 (t, J=6 Hz, 4H), 2.23 (t, J=2.4 Hz, 1H), 1.79-1.69 (m, 4H).

3-((3-(bis(4-methoxyphenyl)(phenyl)methoxy)propyl)(prop-2-yn-1-yl)amino) propan-1-ol, 2'. Reaction was performed from 9.8 mmol of 2". Product was extracted twice with DCM from a 10% Na$_2$CO$_3$ aqueous solution, washed once with a 10% Na$_2$CO$_3$ aqueous solution, dried over MgSO$_4$, filtered and solvent was evaporated under reduced pressure (40° C.). The crude product was loaded on celite and purified using the combiFlash system with a 80 g SiO$_2$ Gold column. Hexanes/TEA (100:1) and ethyl acetate were used in a gradient from 0 to 50% EtOAc. A clear greenish oil was isolated (1.77 g, 38%). HRMS (ESI-QTOF) m/z: [M+Na]$^+$ Calcd for C$_{30}$H$_{35}$O$_4$NNa 496.2458; Found 496.2448. $^1$H NMR (500 MHz, CDCl$_3$): δ (ppm) 7.45 (d, J=7 Hz, 2H), 7.35-7.29 (m, 6H), 7.23 (t, J=7 Hz, 1H), 6.85 (d, J=9 Hz, 4H), 4.33 (br, 1H), 3.82 (s, 6H), 3.77 (t, J=5 Hz, 2H), 3.47 (s, 2H), 3.13 (t, J=6 Hz, 2H), 2.75 (t, J=6 Hz, 2H), 2.64 (t, J=7 Hz, 2H), 2.23 (s, 1H), 1.80 (quin, J=7 Hz, 2H), 1.69 (quin, J=5 Hz, 2H). $^{13}$C NMR (126 MHz, CDCl$_3$): δ (ppm) 158.4, 145.2, 136.5, 130.0, 128.2, 127.7, 126.6, 113.0, 85.9, 77.9, 73.3, 64.2, 61.5, 55.2, 53.6, 51.1, 41.7, 28.2, 28.0.

3-((3-(bis(4-methoxyphenyl)(phenyl)methoxy)propyl)(prop-2-yn-1-yl)amino) propyl (2-cyanoethyl) diisopropylphosphoramidite, (2). Reaction was performed from 0.48 mmol of 2' and purification was achieved with a 12 g SiO$_2$ Gold column. Hexanes/TEA (10:1) and ethyl acetate were used in a gradient from 0 to 40% EtOAc in ~10 CV. A clear transparent oil was isolated (249 mg, 70%). HRMS (ESI-QTOF) m/z: [M+K]$^+$ Calcd for C$_{39}$H$_{52}$N$_3$O$_5$PK 712.3276; Found 712.3296. $^1$H NMR (500 MHz, CDCl$_3$): δ (ppm) 7.43 (d, J=8 Hz, 2H), 7.33-7.26 (m, 6H), 7.20 (t, J=9 Hz, 1H), 6.82 (d, J=9 Hz, 4H), 3.87-3.74 (m, 2H), 3.79 (s, 6H), 3.71-3.55 (m, 4H), 3.37 (d, J=2 Hz, 2H), 3.09 (t, J=6 Hz, 2H), 2.61-2.54 (m, 6H), 2.14 (t, J=2 Hz, 1H), 1.74 (sex, J=7 Hz, 4H), 1.17 (dd, J=7, 9 Hz, 12H). $^{13}$C NMR (126 MHz, CDCl$_3$): δ (ppm) 158.3, 145.3, 136.6, 130.0, 128.2, 127.7, 126.6, 113.0, 85.9, 78.7, 72.7, 61.9, 61.8, 61.6, 58.4, 58.2, 55.2, 50.8, 50.2, 43.1, 43.0, 41.9, 29.3, 29.3, 28.3, 24.7, 24.6, 24.6, 20.4, 20.3. $^{31}$P NMR (203 MHz, CDCl$_3$): δ (ppm) 147.5.

(2S,3R,4R,5S,6S)-2-(acetoxymethyl)-6-(4-(((3-(bis(4-methoxyphenyl) (phenyl)methoxy)propyl)(3-hydroxypropyl)amino)methyl)-1H-1,2,3-triazol-1-yl)tetra hydro-2H-pyran-3,4,5-triyl triacetate, (3'). Adapted from: Tetrahedron, 2017, 187-203. 1-Azido-1-deoxy-β-D-glucopyranoside tetraacetate (379 mg, 0.80 mmol) and 2' (300 mg, 0.80 mmol, 1 equiv.) were suspended in 1 ml CHCl$_3$ and a tBuOH/water (1:1) mixture (12 ml) was added. Freshly prepared solution of sodium ascorbate (12.1 mg, 0.061 mmol, 0.2 equiv.) in 0.2 ml of water and another of copper sulfate (7.6 mg, 0.030 mmol, 0.1 equiv.) in 0.1 ml of water were sequentially added. Reaction was allowed to stir overnight at room temperature. Product was extracted twice with DCM from 10% Na$_2$CO$_3$ aqueous solution, washed once with a 10% Na$_2$CO$_3$ aqueous solution, dried over MgSO$_4$, filtered and solvent was evaporated under reduced pressure (40° C.). The crude obtained was resuspended in toluene to evaporate remaining tBuOH. 643 mg of a pale golden powder were obtained (95%). LRMS: Calc. exact mass: 846.4 g/mol. Measured (positive mode): 869.3 (M+23), 303.3 (DMT$^+$). $^1$H NMR (500 MHz, CDCl$_3$): δ (ppm) 7.69 (s, 1H), 7.41 (d, J=7 Hz, 2H), 7.32-7.26 (m, 6H), 7.21-7.19 (m, 1H), 6.82 (d, J=9 Hz, 4H), 5.83-5.79 (m, 1H), 5.43-5.37 (m, 2H), 5.28-5.22 (m, 1H), 4.30 (dd, J=5, 13 Hz, 1H), 4.14 (dd, J=2, 13 Hz, 1H), 3.99-3.95 (m, 1H), 3.82-3.75 (m, 2H), 3.79 (s, 6H), 3.71 (t, J=5 Hz, 2H), 3.09 (t, J=6 Hz, 2H), 2.68-2.60 (m, 2H), 2.60-2.51 (m, 2H), 2.07 (s, 6H), 2.03 (s, 3H), 1.83 (quin, J=6 Hz, 2H), 1.79 (s, 3H), 1.75-1.63 (m, 2H). $^{13}$C NMR (126 MHz, CDCl$_3$): δ (ppm) 170.7, 170.0, 169.5, 169.0, 158.5, 145.6, 145.4, 136.6, 130.2, 128.3, 127.9, 126.8, 121.1, 113.2, 86.0, 75.4, 72.7, 70.5, 67.9, 64.0, 61.6, 55.3, 53.6, 51.1, 48.7, 28.3, 27.8, 20.8, 20.7, 20.7, 20.2.

(2S,3R,4R,5S,6S)-2-(acetoxymethyl)-6-(4-(((3-(bis(4-methoxyphenyl) (phenyl)methoxy)propyl)(3-(((2-cyanoethoxy)(diisopropylamino)phosphanyl)oxy) propyl)amino)methyl)-1H-1,2,3-triazol-1-yl)tetrahydro-2H-pyran-3,4,5-triyl triacetate, (3). Reaction was performed from 0.22 mmol of 3'. Purification was achieved with a 12 g SiO$_2$ "Gold" column. Hexanes/TEA (10:1) and ethyl acetate were used in a gradient from 0 to 50% EtOAc in ~10 CV. A white crystalline powder was isolated (162 mg, 70%). HRMS (ESI-QTOF) m/z: [M+H]$^+$ Calcd for C$_{53}$H$_{72}$N$_6$O$_{14}$P 1047.4839; Found 1047.4866. $^1$H NMR (500 MHz, CDCl$_3$): δ (ppm) 7.60 (s, 1H), 7.42 (d, J=8 Hz, 2H), 7.32-7.26 (m, 6H), 7.22-7.18 (m, 1H), 6.82 (d, J=9 Hz, 4H), 5.82-5.77 (m, 1H), 5.44-5.37 (m, 2H), 5.27-5.23 (m, 1H), 4.30 (dd, J=5, 13 Hz, 1H), 4.12 (dd, J=2, 13 Hz, 1H), 3.99-3.95 (m, 1H), 3.85-3.72 (m, 10H), 3.70-3.63 (m, 1H), 3.62-6.54 (m, 2H), 3.08 (t, J=6 Hz, 2H), 2.59 (t, J=7 Hz, 2H), 2.53-2.48 (m, 4H), 2.07 (s, 3H), 2.06 (s, 3H), 2.03 (s, 3H), 1.82-1.73 (m, 7H), 1.16 (dd, J=7, 10 Hz, 12H). $^{13}$C NMR (126 MHz, CDCl$_3$): δ (ppm) 170.7, 170.1, 169.5, 168.8, 158.5, 146.3, 145.5, 136.7, 130.2, 128.3, 127.9, 126.7, 120.9, 117.9, 113.1, 85.9, 85.9, 75.3, 72.9, 70.4, 67.9, 62.1, 62.0, 61.7, 58.5, 58.4, 55.4, 50.8, 50.4, 48.7, 43.2, 43.1, 29.1, 28.0, 24.8, 24.8, 24.8, 24.7, 20.8, 20.7, 20.7, 20.5, 20.5, 20.2. $^{31}$P NMR (203 MHz, CDCl$_3$): δ (ppm) 147.3, 147.3 (two diastereoisomers).

Tert-butyl bis(3-hydroxypropyl)glycinate, 11'''. To a solution of glycine tert-butyl ester hydrochloride (2.57 g, 15.3 mmol) in acetonitrile were added KHCO$_3$ (4.60 g, 45.9 mmol, 3 equiv.), KI (254 mg, 1.53 mmol, 0.1 equiv.) and 3-bromo-1-propanol (2.77 ml, 30.6 mmol, 2 equiv.) under stirring. Temperature was raised until a reflux of acetonitrile was reached and left under stirring overnight. The reaction was followed by TLC. After completion, solvent was evaporated under reduced pressure (40° C.). Product was extracted twice with ethyl acetate from 10% Na$_2$CO$_3$ aqueous solution, washed once with a 10% Na$_2$CO$_3$ aqueous solution, dried over MgSO$_4$, filtered and solvent was evaporated under reduced pressure (40° C.). Compound obtained was a pale yellow oil found to be pure up to 90% (NMR) and was used as is for the next step (3.56 g, 94%). LRMS Calc. exact mass: 247.2 g/mol. Measured (positive mode): 248.1 (M+1), 270.1 (M+23). $^1$H NMR (500 MHz, CDCl$_3$): δ (ppm) 3.77 (t, J=6 Hz, 4H), 3.18 (s, 2H), 2.36 (t, J=6 Hz, 4H), 1.72 (quin., J=6 Hz, 4H), 1.47 (s, 9H).

Tert-butyl N-(3-(bis(4-methoxyphenyl)(phenyl)methoxy) propyl)-N-(3-hydroxy propyl)glycinate, 11". Reaction was performed from 14.4 mmol of 11'''. Product was extracted twice with DCM from a 10% Na$_2$CO$_3$ aqueous solution, washed once with a 10% Na$_2$CO$_3$ aqueous solution, dried over MgSO$_4$, filtered and solvent was evaporated under reduced pressure (40° C.). The crude product was loaded on celite and purified using the combiFlash system with a 220 g SiO$_2$ Gold column. Hexanes/TEA (10:1) and ethyl acetate were used in a gradient from 0 to 35% EtOAc (~25CV). A clear yellow oil was isolated (2.96 g, 37%). HRMS (ESI-QTOF) m/z: [M+Na]$^+$ Calcd for C$_{33}$H$_{43}$NO$_6$Na 572.2983; Found 572.2978. $^1$H NMR (500 MHz, CDCl$_3$): δ (ppm) 7.42 (d, J=7 Hz, 2H), 7.32-7.26 (m, 6H), 7.21-7.18 (m 1H), 6.82 (d, J=9 Hz, 4H), 4.54 (br, 1H), 3.79 (s, 6H), 3.74 (t, J=5 Hz, 2H), 3.19 (s, 2H), 3.09 (t, J=6 Hz, 2H), 2.70 (t, J=6 Hz, 2H), 2.64-2.61 (m, 2H), 1.79 (quin, J=8 Hz, 2H), 1.65 (quin, J=5 Hz, 2H), 1.46 (s, 9H). $^{13}$C NMR (126 MHz, CDCl$_3$): δ (ppm) 170.7, 158.5, 145.3, 136.6, 130.1, 128.3, 127.9, 126.8, 113.2, 86.0, 81.5, 63.5, 61.8, 56.6, 55.3, 54.0, 51.8, 28.6, 28.2, 27.9.

Sodium N-(3-(bis(4-methoxyphenyl)(phenyl)methoxy) propyl)-N-(3-hydroxy propyl)glycinate, 11'. Compound 11" (260 mg, 0.47 mmol) was dissolved in about 2 ml of methanol. To the mixture was added 25 ml of 0.4M NaOH in MeOH/water 4:1. The reaction mixture was left under stirring for 3 h at 65° C. Reaction was monitored by TLC. When higher mobility spot disappeared, methanol was evaporated under reduced pressure (60° C.) until a precipitate appears but a small amount of water remains. Precipitate was filtered and quickly washed four times with cold water. The solid was suspended in MeOH, solvent was evaporated under reduced pressure (40° C.). The obtained solid was resuspended in DCM, dried over MgSO$_4$, solution was filtered and solvent was evaporated under reduced pressure (40° C.) to obtain a white to pale yellow solid (206 mg, 85%). NB: An alternate protocol involved a work-up with 2 equivalents of tetrabutylammonium chloride and sodium carbonate solutions. The obtained tetrabutylammonium salt started to degrade after a few days under high vacuum. HRMS (ESI-QTOF) m/z: [M]$^-$ Calcd for C$_{29}$H$_{34}$O$_6$N 492.2392; Found 492.2405. $^1$H NMR (400 MHz, DMSO-d6): δ (ppm) 7.36-7.28 (m, 4H), 7.24-7.19 (m, 5H), 6.88 (d, J=9 Hz, 4H), 3.73 (s, 6H), 3.37 (t, J=6 Hz, 2H), 2.96 (t, J=6 Hz, 2H), 2.71 (s, 2H), 2.43-2.37 (m, 4H), 1.61 (quin, J=7 Hz, 2H), 1.38 (quin, J=6 Hz, 2H). $^{13}$C NMR (126 MHz, DMSO-d6): δ (ppm) 174.4, 157.9, 145.3, 136.1, 129.6, 127.8, 127.6, 126.5, 113.1, 85.2, 61.6, 59.3, 58.2, 55.0, 50.5, 50.1, 29.5, 27.3.

Methyl N-(3-(bis(4-methoxyphenyl)(phenyl)methoxy) propyl)-N-(3-hydroxy propyl)glycyl-L-phenylalaninate, 4'. To a solution of 11' (206 mg, 0.40 mmol) in DMF (5 ml) were successively added anhydrous 1-hydroxybenzotriazole (HOBt) (81 mg, 0.60 mmol, 1.5 equiv.) and N-(3-Dimethylaminopropyl)-N'-ethylcarbodiimide hydrochloride (EDC-Cl) (115 mg, 0.60 mmol, 1.5 equiv.). The pale yellow solution was left under stirring for 5 minutes until complete dissolution of EDC-Cl. Phenylalanine methyl ester hydrochloride (95 mg, 0.44 mmol, 1.1 equiv.) and triethylamine (0.15 ml, 1.04 mmol, 2.6 equiv.) were then successively added. The reaction mixture slowly turned cloudy and was left under vigorous stirring overnight. Solvent was then evaporated under reduced pressure (60° C.). The crude product was loaded on celite and purified using the combi-Flash system with a 12 g SiO$_2$ "Gold" column. Hexanes/TEA (10:1) and ethyl acetate were used in a gradient from 0 to 70% EtOAc in ~12 CV. A clear pale yellow oil was isolated (173 mg, 66%). NB: Interestingly, when the crude in DMF is analyzed using RP-HPLC, conversion yields reached 90% but isolated yields never exceeded 66%. This may be due to issues with column chromatography or to the presence of undesired salts at the end of the previous step. LRMS: Calc. exact mass: 654.33 g/mol. Measured (positive mode): 303.3 (DMT$^+$), 677.3 (M+23). $^1$H NMR (500 MHz, CDCl$_3$): δ (ppm) 7.60 (d, J=8 Hz, 1H), 7.41 (d, J=7 Hz, 2H), 7.31-7.18 (m, 10H), 7.08 (d, J=7 Hz, 2H), 6.83 (d, J=9 Hz, 4H), 4.85 (q, J=8 Hz, 1H), 3.79 (s, 6H), 3.71 (s, 3H), 3.53 (t, J=6 Hz, 2H), 3.15-2.94 (m, 6H), 2.61-2.53 (m, 2H), 2.49-2.43 (m, 2H), 1.68-1.61 (m, 2H), 1.60-1.55 (m, 2H). $^{13}$C NMR (126 MHz, CDCl$_3$): δ (ppm) 172.5, 171.5, 158.5, 145.3, 136.6, 136.2, 130.1, 129.3, 128.7, 128.3, 127.9, 127.2, 126.8, 113.2, 86.0, 61.5, 60.8, 58.8, 55.3, 52.7, 525, 52.4, 52.0, 37.9, 30.2, 28.03.

Methyl N-(3-(bis(4-methoxyphenyl)(phenyl)methoxy) propyl)-N-(3-(((2-cyano ethoxy)(diisopropylamino)phosphanyl)oxy)propyl)glycyl-L-phenylalaninate, 4. Reaction was performed from 0.333 mol of 4'. Purification was achieved with a 12 g SiO$_2$ "Gold" column. Hexanes/TEA (10:1) and ethyl acetate were used in a gradient from 0 to 40% EtOAc in ~12 CV. A clear transparent oil was isolated (195 mg, 68%). HRMS (ESI-QTOF) m/z: [M+Na]$^+$ Calcd for C$_{48}$H$_{63}$N$_4$O$_8$PNa 877.4276; Found 877.4257. $^1$H NMR (500 MHz, CDCl$_3$): δ (ppm) 7.64 (d, J=8 Hz, 1H), 7.40 (d, J=7 Hz, 2H), 7.31-7.15 (m, 10H), 7.07 (d, J=7 Hz, 2H), 6.82 (d, J=9 Hz, 4H), 4.83 (q, J=8 Hz, 1H), 3.84-3.76 (m, 8H), 3.68 (s, 3H), 3.60-3.50 (m, 2H), 3.16-3.12 (m, 1H), 3.05-2.97 (m, 5H), 2.58 (td, J=2, 7 Hz, 2H) 2.55-2.47 (m, 4H), 1.67-1.59 (m, 4H), 1.17 (dd, J=7, 9 Hz, 12H). $^{13}$C NMR (126 MHz, CDCl$_3$): δ (ppm) 171.9, 11.5, 158.2, 145.3, 136.6, 136.2, 130.1, 129.3, 128.7, 128.3, 127.9, 127.2, 126.8, 113.2, 86.0, 61.5, 58.5, 55.3, 53.0, 52.7, 52.5, 52.3, 43.2, 43.1, 38.0, 29.3, 28.2, 24.8, 24.7, 20.5, 20.5. $^{31}$P NMR (203 MHz, CDCl$_3$): δ (ppm) 147.6.

Methyl N-(3-(bis(4-methoxyphenyl)(phenyl)methoxy) propyl)-N-(3-hydroxy propyl)glycyl-L-histidinate, 5'. Compound 11" (484 mg, 0.88 mmol, 1 equiv.) was dissolved in about 2 ml of methanol. To the mixture was added 25 ml of 0.4M NaOH in MeOH/water 4:1. The reaction mixture was left under stirring for 3 h at 65° C. Reaction was monitored by TLC. When the higher mobility spot disappeared, methanol was evaporated under reduced pressure (60° C.) until a precipitate appears but a small amount of water remains. DCM is added to the obtained solution and 2 equiv. of tetrabutylammonium chloride (489 mg, 1.76 mmol) were added. Two extractions with DCM from sat. Na$_2$CO$_3$ solution were performed followed by one washing with 10% Na$_2$CO$_3$ solution. Organic fractions were combined, dried over MgSO$_4$, filtered and the solvent was evaporated under reduced pressure (40° C.). The tetrabutylammonium carboxylate salt obtained was suspended in anhydrous DMF (5 ml). Anhydrous HOBt (154 mg, 1.14 mmol, 1.3 equiv.) and EDC-Cl (219 mg, 1.14 mmol, 1.3 equiv.) were successively added under argon. The solution was left under stirring for 5 minutes until complete dissolution of EDC-Cl. Histidine methyl ester dihydrochloride (224 mg, 0.92 mmol, 1.05 equiv.) and triethylamine (0.61 ml, 4.4 mmol, 5 equiv.) were then successively added. The reaction mixture was left under vigorous stirring overnight. Product was extracted twice with DCM from 10% Na₂CO₃ aqueous solution, washed once with a 10% Na₂CO₃ aqueous solution, dried over MgSO₄, filtered and solvent was evaporated under reduced pressure (60° C.). The crude product was loaded on celite and purified using the combiFlash system with a SiO2 "Gold" column pretreated with 0.1% TEA in DCM. DCM/TEA (100:0.1) and DCM/Methanol/TEA (90:10:0.1) were used in a gradient. Product was extracted again to remove triethylammonium salts, twice with DCM from 10% Na₂CO₃ aqueous solution, washed once with a 10% Na₂CO₃ aqueous solution, dried over MgSO₄, filtered and solvent was evaporated under reduced pressure (60° C.). A white solid was isolated (233 mg, 0.361 mmol, 41%). LRMS: Calc. exact mass: 644.32 g/mol. Measured (positive mode): 667.2 (M+23). $^1$H NMR (500 MHz, CDCl₃): δ (ppm) 9.17 (bs 1H), 8.16 (bs, 1H), 7.47 (d, J=1 Hz, 1H), 7.40-7.39 (m, 2H), 7.29-7.26 (m, 6H), 7.22-7.18 (m, 1H), 6.81 (d, J=9 Hz, 4H), 6.77 (s, 1H), 4.86-4.82 (m, 1H), 3.79 (s, 6H), 3.73-3.69 (m, 5H), 3.14-3.04 (m, 6H), 2.62-2.54 (m, 4H), 1.73-1.65 (m, 4H). $^{13}$C NMR (126 MHz, DMSO): δ (ppm) 171.6, 170.7, 157.9, 145.2, 136.0, 135.0, 129.6, 127.8, 127.6, 126.6, 113.1, 85.2, 61.2, 58.9, 57.9, 55.0, 51.8, 51.6, 51.4, 45.7, 30.0.

27.2. Methyl N-(3-(bis(4-methoxyphenyl)(phenyl) methoxy)propyl)-N-(3-(((2-cyano ethoxy)(diisopropylamino)phosphanyl)oxy)propyl)glycyl-L-histidinate (5). Compound 5' was suspended in acetonitrile and solvent was evaporated under reduced pressure (60° C.). The operation was repeated once and the dried compound was kept under high vacuum for at least 5 hours. In an oven-dried flask, compound 5' (154 mg, 0.239 mmol, 1 equiv.) was then dissolved in anhydrous DCM (5 ml) and 0.21 ml of dry DIPEA (1.2 mmol, 5 equiv.) were added under stirring. CEP-Cl (0.06 ml, 0.2 mmol, 1.1 equiv.) was added slowly and the reaction was allowed to stir under inert gas at room temperature for 2 hours. Two fast extractions with DCM from a 10% Na₂CO₃ aqueous solution were performed. Organic fractions were combined, dried over MgSO₄, filtered and the solvent was evaporated under reduced pressure (40° C.). The crude product was loaded on celite and purified using the combiFlash system with a SiO₂ "Gold" column pretreated with 1% TEA in hexanes. Hexanes/TEA (100:1) and ethyl acetate were used in a gradient. A white solid was isolated (110 mg, 0.130 mmol, 54%). HRMS (ESI-QTOF) m/z: [M+Na]$^+$ Calcd for C₄₅H₆₁N₆O₈PNa 867.4181; Found 867.4164. $^1$H NMR (500 MHz, CDCl₃): δ (ppm) 9.41 (bs 1H), 8.04 (bs, 1H), 7.47 (s, 1H), 7.40-7.39 (m, 2H), 7.29-7.26 (m, 6H), 7.21-7.18 (m, 1H), 6.81 (d, J=9 Hz, 4H), 6.73 (s, 1H), 4.80-4.77 (m, 1H), 3.88-3.55 (m, 15H), 3.11-3.03 (m, 6H), 2.63-2.52 (m, 6H), 1.72-1.63 (m, 4H), 1.17 (t, J=6 Hz, 12H). $^{13}$C NMR (126 MHz, CDCl₃): δ (ppm) 158.5, 145.3, 136.6, 135.2, 130.1, 128.3, 127.9, 126.8, 113.2, 86.0, 62.0, 61.7, 58.7, 58.2, 58.1, 58.0, 55.3, 53.0, 52.9, 52.6, 52.4, 52.2, 51.8, 51.1, 45.6, 43.2, 43.1, 29.8, 29.4, 28.1, 24.8, 24.8, 24.8, 24.7, 20.6, 20.6. $^{31}$P NMR (203 MHz, CDCl₃): δ (ppm) 147.6 147.4.

N-(2-aminoethyl)-2-((3-(bis(4-methoxyphenyl)(phenyl) methoxy)propyl)(3-hydroxypropyl)amino)acetamide (6"). In a round bottom flask, 350 mg (0.64 mmol) of 11" were dissolved in 5 ml of ethylenediamine. Solution was left under vigorous stirring under reflux for 48 h. Product was extracted twice with DCM from 10% Na₂CO₃ aqueous solution, washed once with a saturated Na₂CO₃ aqueous solution, dried over MgSO₄, filtered and solvent was evaporated under reduced pressure (40° C.) to obtain a yellow oil (299 mg, 88%). HRMS (ESI-QTOF) m/z: [M+Na]$^+$ Calcd for C₃₁H₄₁N₃O₅Na 558.29384; Found 558.29354. $^1$H NMR (500 MHz, CDCl₃): δ (ppm) 7.54 (t, J=6 Hz, 1H), 7.42-7.40 (m, 2H), 7.31-7.26 (m, 6H), 7.22-7.20 (m, 1H), 6.82 (d, J=9 Hz, 4H), 3.79 (s, 6H), 3.62 (t, J=6 Hz, 2H), 3.25 (q, J=5 Hz, 2H), 3.09 (t, J=6 Hz, 2H), 3.04 (s, 2H), 2.78 (t, J=6 Hz, 2H), 2.57 (q, J=6 Hz, 4H), 1.79-1.71 (m, 2H), 1.67-1.62 (m, 2H). $^{13}$C NMR (126 MHz, CDCl₃): δ (ppm) 171.9, 158.5, 145.3, 136.5, 130.1, 128.2, 127.9, 126.8, 113.2, 86.1, 61.6, 59.5, 59.2, 55.4, 52.3, 51.1, 41.5, 41.1, 59.7, 27.8.

N-(2-(2-((3-(bis(4-methoxyphenyl)(phenyl)methoxy)propyl)(3-hydroxy propyl)amino)acetamido)ethyl)-2,2,2-trifluoroacetamide, (6'). In a round bottom flask, 648 mg (1.21 mmol, 1 equiv.) of 6" were dissolved in 10 ml of DCM and 1 ml of pyridine. Ethyl trifluoroacetate (0.15 ml, 1.3 mmol, 1.05 equiv.) was slowly added under vigorous stirring. Reaction was left under stirring overnight. Product was extracted twice with DCM from 10% Na₂CO₃ aqueous solution, washed once with a 10% Na₂CO₃ aqueous solution. Organic fractions were combined, dried over MgSO₄, filtered and the solvent was evaporated under reduced pressure (40° C.). The crude product was loaded on celite and purified using the combiFlash system with a SiO₂ "Gold" column pretreated with 0.1% TEA in DCM. DCM/TEA (100:0.1) and DCM/Methanol/TEA (90:10:0.1) were used in a gradient. A clear yellow wax was isolated (485 mg, 0.768 mmol, 63%). LRMS: Calc. exact mass: 631.29 g/mol. Measured (negative mode): 630.24 (M−1), $^1$H NMR (500 MHz, DMSO-d6): δ (ppm) 9.38 (s, 1H), 7.76 (s, 1H), 7.37-7.35 (m, 2H), 7.31-7.28 (m, 2H), 7.24-7.19 (m, 5H), 6.87 (d, J=9 Hz, 4H), 4.43 (s, 1H), 3.73 (s, 6H), 3.40 (t, J=6 Hz, 2H), 3.22 (s, 4H), 2.96 (t, J=6 Hz, 2H), 2.91 (s, 2H), 2.47-2.44 (m, 4H), 1.69-1.64 (m, 2H), 1.54-1.48 (m, 2H). $^{13}$C NMR (126 MHz, DMSO-d6): δ (ppm) 171.2, 158.0, 156.6, 156.3, 145.2, 136.0, 129.6, 127.8, 127.6, 126.6, 117.0, 114.7, 113.1, 85.2, 61.2, 58.9, 57.8, 55.0, 51.5, 51.5, 37.2, 29.8, 27.1. $^{19}$F NMR (471 MHz, DMSO-d6): δ (ppm) ~74.5.

3-((3-(bis(4-methoxyphenyl)(phenyl)methoxy)propyl)(2-oxo-2-((2-(2,2,2-trifluoroacetamido)ethyl)amino)ethyl) amino)propyl (2-cyanoethyl) diisopropylphosphoramidite (6). Reaction was performed from 0.744 mmol of 6'. The crude product was loaded on celite and purified using the combiFlash system with a SiO₂ "Gold" column pretreated with 1% TEA in hexanes. Hexanes/TEA (100:1) and ethyl acetate/TEA (100/1) were used in a gradient. A white waxy solid was isolated (396 mg, 0.476 mmol, 64%). HRMS (APCI-QTOF) m/z: [M+H]$^+$ Calcd for C₄₂H₅₈N₅O₇PF₃ 832.40205; Found 832.40168. $^1$H NMR (500 MHz, CDCl₃): δ (ppm) 8.18 (s, 1H), 7.63-7.61 (m, 1H), 7.41-7.39 (m, 2H), 7.29-7.26 (m, 6H), 7.22-7.19 (m, 1H), 6.82 (d, J=9 Hz, 4H), 3.85-3.81 (m, 1H), 3.79 (s, 6H), 3.75-3.55 (m, 5H), 3.37-3.34 (m, 4H), 3.08 (t, J=6 Hz, 2H), 3.05 (s, 2H), 2.61-2.58 (m, 6H), 1.75-1.71 (m, 4H), 1.17 (t, J=7 Hz, 12H). $^{13}$C NMR (126 MHz, CDCl₃): δ (ppm) 174.6, 158.6, 157.8, 157.5, 145.2, 136.4, 130.1, 138.2, 127.9, 126.9, 117.9, 117.1, 114.8, 113.2, 86.1, 61.8, 61.7, 61.4, 58.4, 58.2, 58.1, 55.4, 52.4, 52.3, 43.2, 43.1, 42.2, 38.3, 28.9, 28.9, 27.8, 24.8, 24.8, 24.7, 24.7, 20.6, 20.6. $^{19}$F NMR (471 MHz, CDCl₃): δ (ppm) ~76.0. $^{31}$P NMR (203 MHz, CDCl₃): δ (ppm) 147.6.

3-(((1-(Anthracen-9-ylmethyl)-1H-1,2,3-triazol-4-yl) methyl) (3-(bis(4-methoxyphenyl)(phenyl)methoxy)propyl) amino)propan-1-ol (7). In a 10 ml round-bottom flask covered with an aluminum foil, 9-(Azidomethyl)anthracene (257 mg, 0.80 mmol, 0.95 equiv.) and 2' (550 mg, 1.16 mmol, 1 equiv.) were suspended in 1.5 ml CHCl₃ and a tBuOH/water (1:1) mixture (12 ml) was added. Freshly prepared solution of sodium ascorbate (46.0 mg, 0.232 mmol, 0.20 equiv.) in 0.3 ml of water and another of copper sulfate (29.0 mg, 0.116 mmol, 0.1 equiv.) in 0.15 ml of water were sequentially added. Reaction was allowed to stir for 6 h at room temperature. Product was extracted twice with DCM from 10% $Na_2CO_3$ aqueous solution, washed once with a 10% $Na_2CO_3$ aqueous solution, dried over $MgSO_4$, filtered and solvent was evaporated under reduced pressure (40° C.). The crude obtained was resuspended in toluene to evaporate remaining tBuOH. 643 mg of a dark yellow/brown solid were obtained (714 mg, 1.01 mmol, 87%). The compound was kept away from light. HRMS (APCI-QTOF) m/z: [M+Cl]− Calcd for $C_{45}H_{46}N_4O_4Cl$ 741.32131; Found 741.32122. $^1H$ NMR (500 MHz, $CDCl_3$): δ (ppm) 8.56 (s, 1H), 8.26 (d, J=9 Hz, 2H), 8.06 (d, J=8 Hz, 2H), 7.54-7.49 (m, 4H), 7.38-7.37 (m, 2H), 7.27-7.24 (m, 7H), 7.20-7.17 (m, 1H), 7.06 (s, 1H), 6.80 (d, J=9 Hz, 4H), 6.50 (s, 2H), 3.78 (s, 6H), 3.60 (s, 2H), 3.49 (t, J=5 Hz, 2H), 2.99 (t, J=6 Hz, 2H), 2.54 (t, J=6 Hz, 2H), 2.48-2.45 (m, 2H), 1.72-1.66 (m, 2H), 1.55 (quint, J=5 Hz, 2H). $^{13}C$ NMR (126 MHz, $CDCl_3$): δ (ppm) 158.4, 145.3, 144.6, 136.6, 131.5, 130.9, 130.1, 129.9, 129.6, 128.2, 127.8, 127.7, 126.7, 125.5, 124.0, 123.1, 122.1, 113.1, 85.9, 63.9, 61.6, 55.3, 53.6, 51.0, 48.8, 46.6, 28.0, 27.6.

(3-(((1-(Anthracen-9-ylmethyl)-1H-1,2,3-triazol-4-yl) methyl)(3-(bis(4-methoxyphenyl) (phenyl)methoxy)propyl) amino)propyl (2-cyanoethyl) diisopropylphosphoramidite (7). Compound 7' was suspended in toluene and solvent was evaporated under reduced pressure (60° C.). The operation was repeated once and the dried compound was kept under high vacuum for at least 5 hours. In an oven-dried flask covered with aluminum foil, compound 9 (714 mg, 1.01 mmol, 1 equiv.) was then dissolved in anhydrous DCM (10 ml) and 0.88 ml of dry DIPEA (5.1 mmol, 5 equiv.) were added under stirring. CEP-Cl (0.29 ml, 1.3 mmol, 1.3 equiv.) was added slowly and the reaction was allowed to stir under inert gas at room temperature for 2 hours. Two fast extractions with DCM from a 10% $Na_2CO_3$ aqueous solution were performed. Organic fractions were combined, dried over $MgSO_4$, filtered and the solvent was evaporated under reduced pressure (40° C.). The crude product was loaded on celite and purified using the combiFlash system with a $SiO_2$ "Gold" column pretreated with 1% TEA in hexanes. Hexanes/TEA (100:1) and ethyl acetate were used in a gradient. A white solid was isolated (690 mg, 0.855 mmol, 85%). This compound was stored away from light. HRMS (APCI-QTOF) m/z: [M+Cl]− Calcd for $C_{54}H_{63}N_6O_5PCl$ 941.42916; Found 941.42839. $^1H$ NMR (500 MHz, $CDCl_3$): δ (ppm) 8.57 (s 1H), 8.26-8.23 (m, 2H), 8.07-8.05 (m, 2H), 7.53-7.47 (m, 4H), 7.37-7.35 (m, 2H), 7.21-7.15 (m, 7H), 7.06 (s, 1H), 6.78 (d, J=9 Hz, 4H), 6.49 (s, 2H), 3.77-3.66 (m, 8H), 3.57 (s, 2H), 3.56-3.44 (m, 4H), 2.94 (t, J=6 Hz, 2H), 2.53 (t, J=6 Hz, 2H), 2.45-2.39 (m, 4H), 1.65-1.58 (m, 4H), 1.14 (d, J=6 Hz, 6H), 1.06 (d, J=7 Hz, 6H). $^{13}C$ NMR (126 MHz, $CDCl_3$): δ (ppm) 158.4, 145.7, 145.4, 136.7, 131.6, 130.9, 130.1, 129.9, 129.5, 128.3, 127.8, 127.7, 126.7, 125.5, 124.1, 123.2, 121.9, 117.8, 113.1, 85.8, 62.0, 61.9, 61.6, 58.5, 58.3, 55.3, 50.9, 50.4, 49.1, 46.6, 43.1, 43.0, 28.8, 28.7, 27.7, 24.8, 24.7, 24.7, 24.6, 20.5, 20.4. $^{31}P$ NMR (203 MHz, $CDCl_3$): δ (ppm) 147.2.

Methyl N-(3-(bis(4-methoxyphenyl)(phenyl)methoxy) propyl)-N-(3-hydroxypropyl)glycyl-L-tryptophanate), (8'). Compound 11' (484 mg, 0.88 mmol, 1 equiv.) was dissolved in about 2 ml of methanol. To the mixture was added 25 ml of 0.4M NaOH in MeOH/water 4:1. The reaction mixture was left under stirring for 3 h at 65° C. Reaction was monitored by TLC. When higher mobility spot disappeared, methanol was evaporated under reduced pressure (60° C.) until a precipitate appears but a small amount of water remains. DCM is added to the obtained solution and 2 equiv. of tetrabutylammonium chloride (489 mg, 1.76 mmol) were added. Two extractions with DCM from sat. $Na_2CO_3$ solution were performed followed by one washing with 10% $Na_2CO_3$ solution. Organic fractions were combined, dried over $MgSO_4$, filtered and the solvent was evaporated under reduced pressure (40° C.). The tetrabutylammonium carboxylate salt obtained was suspended in DMF (5 ml). Anhydrous HOBt (154 mg, 1.14 mmol, 1.3 equiv.) and EDC-Cl (219 mg, 1.14 mmol, 1.3 equiv.) were successively added. The solution was left under stirring for 5 minutes until complete dissolution of EDC-Cl. Tryptophan methyl ester hydrochloride (235 mg, 0.92 mmol, 1.05 equiv.) and triethylamine (0.61 ml, 4.4 mmol, 5 equiv.) were then successively added. The reaction mixture was left under vigorous stirring overnight. Solvent was evaporated under reduced pressure (60° C.). The crude product was loaded on celite and purified using the combiFlash system with a $SiO_2$ "Gold" column pretreated with 0.1% TEA in DCM. DCM/TEA (100:0.1) and DCM/Methanol/TEA (90:10:0.1) were used in a gradient. A pale yellow solid was isolated (260 mg, 0.374 mmol, 43%). HRMS (ESI-QTOF) m/z: [M+H]+ Calcd for $C_{41}H_{48}N_3O_7$ 694.34868; Found 694.34783. $^1H$ NMR (500 MHz, $CDCl_3$): δ (ppm) 8.36 (s, 1H), 7.66 (d, J=8 Hz, 1H), 7.52 (d, J=8 Hz, 1H), 7.43-7.41 (m, 2H), 7.31-7.21 (m, 8H), 7.13 (t, J=7 Hz, 1H), 7.08 (t, J=7 Hz, 1H), 6.92 (d, J=2 Hz, 1H), 6.83 (d, J=9 Hz, 4H), 4.92-4.88 (m, 1H), 3.78 (s, 6H), 3.68 (s, 3H), 3.38-3.26 (m, 4H), 3.09-2.96 (m, 4H), 2.34-2.52 (m, 4H), 1.63-1.52 (m, 2H), 1.47-1.39 (m, 2H). $^{13}C$ NMR (126 MHz, $CDCl_3$): δ (ppm) 172.7, 171.7, 158.4, 145.3, 136.5, 136.2, 130.1, 128.2, 127.9, 127.7, 126.8, 122.9, 122.2, 119.6, 118.6, 113.1, 111.3, 109.9, 86.0, 61.5, 60.5, 58.7, 55.3, 52.5, 52.5, 52.1, 52.0, 30.1, 27.8, 27.4.

Methyl N-(3-(bis(4-methoxyphenyl)(phenyl)methoxy) propyl)-N-(3-(((2-cyanoethoxy) (diisopropylamino)phosphanyl)oxy)propyl)glycyl-L-tryptophanate, (8). Compound 8' was suspended in acetonitrile and solvent was evaporated under reduced pressure (60° C.). The operation was repeated once and the dried compound was kept under high vacuum for at least 5 hours. In an oven-dried flask, compound 8' (254 mg, 0.353 mmol, 1 equiv.) was then dissolved in anhydrous DCM (6 ml) and 0.31 ml of dry DIPEA (1.8 mmol, 5 equiv.) were added under stirring. CEP-Cl (0.10 ml, 0.46 mmol, 1.3 equiv.) was added slowly and the reaction was allowed to stir under inert gas at room temperature for 2 hours. Two fast extractions with DCM from a 10% $Na_2CO_3$ aqueous solution were performed. Organic fractions were combined, dried over $MgSO_4$, filtered and the solvent was evaporated under reduced pressure (40° C.). The crude product was loaded on celite and purified using the combiFlash system with a $SiO_2$ "Gold" column pretreated with 1% TEA in hexanes. Hexanes/TEA (100:1) and ethyl acetate were used in a gradient. A white solid was isolated (286 mg, 0.320 mmol, 91%). HRMS (ESI-QTOF) m/z: [M+H]+ Calcd for $C_{50}H_{65}N_5O_8P$ 894.45653: Found 894.45527. $^1H$ NMR (500 MHz, $CDCl_3$): δ (ppm) 8.54 (s, 1H), 7.72 (d, J=8 Hz, 1H), 7.50 (d, J=8 Hz, 1H), 7.41-7.40 (m, 2H), 7.29-7.19 (m, 8H), 7.11 (t, J=7 Hz, 1H), 7.05 (t, J=7 Hz, 1H), 6.92 (m, 1H), 6.81 (d, J=9 Hz, 4H), 4.88-4.85 (m, 1H), 3.83-3.69 (m, 8H), 3.64 (s, 3H), 3.62-3.42 (m, 4H), 3.35-3.24 (m, 2H), 3.06-2.95 (m, 4H), 2.55 (t, J=5 Hz, 2H), 2.49-2.44 (m, 4H), 1.55-1.47 (m, 4H), 1.20-1.15 (m, 12H). $^{13}C$ NMR (126 MHz, $CDCl_3$): δ (ppm) 172.1, 171.5, 158.3, 145.2, 136.4, 136.4, 136.1, 129.9, 128.1, 127.7, 127.5, 126.6, 122.8, 121.9, 119.3, 118.4, 117.8, 117.8, 113.0, 111.3, 109.7, 109.7, 85.8, 61.8, 61.7, 61.6, 61.6, 61.3, 58.5, 58.5, 58.2, 58.1, 58.0, 58.0, 55.1, 52.6, 52.4, 52.2, 52.0, 43.0, 42.9, 29.0, 28.9, 27.9, 27.8, 27.4, 24.6, 24.6, 24.6, 24.6, 20.3, 20.3. $^{31}$P NMR (203 MHz, CDCl$_3$): δ (ppm) 147.5 147.4.

methyl N-(3-(bis(4-methoxyphenyl)(phenyl)methoxy) propyl)-N-(3-hydroxypropyl)glycyl-L-phenylalanyl-L-phenylalaninate, (9'). Compound 11' (484 mg, 0.88 mmol, 1 equiv.) was dissolved in about 2 ml of methanol. To the mixture was added 25 ml of 0.4M NaOH in MeOH/water 4:1. The reaction mixture was left under stirring for 3 h at 65° C. Reaction was monitored by TLC. When higher mobility spot disappeared, methanol was evaporated under reduced pressure (60° C.) until a precipitate appears but a small amount of water remains. DCM is added to the obtained solution and 2 equiv. of tetrabutylammonium chloride (489 mg, 1.76 mmol) were added. Two extractions with DCM from sat. Na$_2$CO$_3$ solution were performed followed by one washing with 10% Na$_2$CO$_3$ solution. Organic fractions were combined, dried over MgSO$_4$, filtered and the solvent was evaporated under reduced pressure (40° C.). The tetrabutylammonium carboxylate salt obtained was suspended in DMF (5 ml). Anhydrous HOBt (154 mg, 1.14 mmol, 1.3 equiv.) and EDC-Cl (219 mg, 1.14 mmol, 1.3 equiv.) were successively added. The solution was left under stirring for 5 minutes until complete dissolution of EDC-Cl. L-Phenylalanyl-L-phenylalanine methyl ester hydrochloride (335 mg, 0.92 mmol, 1.05 equiv.) and triethylamine (0.61 ml, 4.4 mmol, 5 equiv.) were then successively added. The reaction mixture was left under vigorous stirring overnight. Solvent was evaporated under reduced pressure (60° C.). The crude product was loaded on celite and purified using the combiFlash system with a SiO$_2$ "Gold" column pretreated with 0.1% TEA in hexanes. Hexanes/TEA (100:0.1) and ethyl acetate were used in a gradient. A white solid was isolated (268 mg, 0.334 mmol, 38%). HRMS (ESI-QTOF) m/z: [M+H]$^+$ Calcd for C$_{48}$H$_{56}$N$_3$O$_8$ 802.4042; Found 802.4062. $^1$H NMR (500 MHz, CDCl$_3$): δ (ppm) 7.76 (d, J=8 Hz, 1H), 7.45-7.44 (m, 2H), 7.34-7.16 (m, 15H), 7.05-7.03 (m, 2H), 6.87-6.84 (m, 4H), 6.60 (d, J=8 Hz, 1H), 4.78 (q, J=8 Hz, 1H), 4.64 (q, J=7 Hz, 1H), 3.80 (s, 6H), 3.68 (s, 3H), 3.59-3.49 (m, 2H), 3.12-2.90 (m, 8H), 2.60-2.41 (m, 4H), 1.65-1.49 (m, 4H). $^{13}$C NMR (126 MHz, CDCl$_3$): δ (ppm) 171.8, 171.5, 170.9, 158.4, 145.2, 136.6, 136.4, 135.8, 130.0, 129.3, 128.6, 128.5, 128.1, 127.8, 127.0, 126.9, 126.7, 113.1, 85.9, 61.4, 60.3, 58.6, 55.2, 54.1, 53.5, 52.3, 52.1, 51.5, 37.8, 37.7, 29.7, 27.7.

methyl N-(3-(bis(4-methoxyphenyl)(phenyl)methoxy) propyl)-N-(3-(((2-cyanoethoxy) (diisopropylamino)phosphanyl)oxy)propyl)glycyl-L-phenylalanyl-L-phenylalaninate, (9). Reaction was performed from 0.048 mmol of 9'. The crude product was loaded on celite and purified using the combiFlash system with a SiO2 "Gold" column pretreated with 1% TEA in hexanes. Hexanes/TEA (100:1) and ethyl acetate were used in a gradient. A white waxy solid was isolated (25 mg, 0.025 mmol, 52%). HRMS (ESI-QTOF) m/z: [M+H]+ Calcd for C$_{57}$H$_{73}$N$_5$O$_9$P 1002.5140; Found 1002.5128. $^1$H NMR (500 MHz, CDCl3): δ (ppm) 7.61 (d, J=8 Hz, 1H), 7.41-7.39 (m, 2H), 7.30-7.26 (m, 6H), 7.22-7.12 (m, 9H), 6.99-6.97 (m, 2H), 6.83-6.80 (m, 4H), 6.49-6.47 (m, 1H), 4.72 (q, J=8 Hz, 1H), 4.58 (q, J=7 Hz, 1H), 3.84-3.72 (m, 8H), 3.65 (s, 3H), 3.61-3.46 (m, 4H), 3.09-2.94 (m, 8H), 2.59-2.56 (m, 2H), 2.49-2.40 (m, 4H), 1.60-1.52 (m, 4H), 1.17 (t, J=7 Hz, 12H). $^{13}$C NMR (126 MHz, CDCl3): δ (ppm) 172.2, 171.5, 170.5, 158.5, 145.3, 136.7, 136.5, 136.5, 135.9, 130.1, 129.4, 129.3, 128.7, 128.6, 128.3, 127.9, 127.2, 127.1, 126.8, 117.8, 113.2, 86.0, 61.9, 61.8, 61.5, 58.4, 58.4, 58.3, 55.3, 54.0, 53.5, 52.9, 52.4, 52.4, 46.3, 43.2, 43.1, 37.9, 37.4, 29.8, 29.0, 29.0, 27.8, 24.8, 24.8, 24.7, 22.7, 20.5, 20.5. $^{31}$P NMR (203 MHz, CDCl$_3$): δ (ppm) 147.5.

N-(2-(2-((3-(bis(4-methoxyphenyl) (phenyl)methoxy) propyl)(3-hydroxypropyl)amino)acetamido)ethyl)-5-((3aS,4S,6aR)-2-oxohexahydro-1H-thieno[3,4-d]imidazol-4-yl) pentanamide, (10'). Biotin (91 mg, 0.373 mmol, 1 equiv.) was suspended in DMF (1 ml). Anhydrous HOBt (66 mg, 0.485 mmol, 1.3 equiv.) and EDC-Cl (93 mg, 0.485 mmol, 1.3 equiv.) were successively added. The solution was left under stirring for 5 minutes until complete dissolution of EDC-Cl. Compound 6'' (200 mg, 0.373 mmol, 1 equiv.) and triethylamine (0.26 ml, 1.9 mmol, 5 equiv.) were dissolved in DMF (1 ml) and incorporated in the stirred reaction medium. The reaction mixture was left under vigorous stirring overnight Product was extracted twice with DCM from 10% Na$_2$CO$_3$ aqueous solution, washed once with a saturated Na$_2$CO$_3$ aqueous solution, dried over MgSO$_4$, filtered and solvent was evaporated under reduced pressure (60° C.). The crude product was loaded on celite and purified using the combiFlash system with a SiO2 "Gold" column pretreated with 0.1% TEA in DCM. DCM/TEA (100:0.1) and DCM/Methanol/TEA (90:10:0.1) were used in a gradient. Product was extracted again to remove triethylammonium salts, once with DCM from 10% Na$_2$CO$_3$ aqueous solution, washed once with a 10% Na$_2$CO$_3$ aqueous solution, dried over MgSO$_4$, filtered and solvent was evaporated under reduced pressure (60° C.). A pale yellow waxy solid was isolated (196 mg, 0.257 mmol, 73%). HRMS (ESI-QTOF) m/z: [M+Na]+ Calcd for C$_{41}$H$_{55}$N$_5$NaO$_7$S 784.3714; Found 784.3696. $^1$H NMR (500 MHz, CDCl$_3$): δ (ppm) 7.71-7.69 (m, 1H), 7.65-7.63 (m, 1H), 7.41-7.39 (m. 2H), 7.30-7.25 (m, 5H), 7.21-7.18 (m, 2H), 6.81 (d, J=9 Hz, 4H), 6.39 (br. s, 1H), 5.28-5.28 (m, 1H), 4.49-4.46 (m, 1H), 4.29-4.26 (m, 1H), 3.78 (s, 6H), 3.65-3.62 (m, 2H), 3.46-3.38 (m, 2H), 3.24-3.15 (m, 2H), 3.10-2.96 (m, 5H), 2.89-2.85 (m, 1H), 2.75-2.70 (m, 1H), 2.61-2.48 (m, 4H), 2.24-2.13 (m, 2H), 1.76-1.58 (m, 8H), 1.43-1.32 (m, 2H). $^{13}$C NMR (126 MHz, CDCl$_3$): δ (ppm) 174.4, 172.9, 164.7, 158.5, 145.2, 136.5, 130.0, 128.2, 127.9, 126.8, 113.1, 86.0, 61.6, 61.4, 60.4, 60.1, 58.6, 55.9, 55.3, 53.5, 52.0, 51.2, 40.8, 39.4, 39.0, 36.0, 30.0, 29.8, 28.2, 28.1, 27.6, 25.6.

3-((3-(bis(4-methoxyphenyl)(phenyl)methoxy)propyl) (2-oxo-2-((2-(5-((3aS,4S,6aR)-2-oxohexahydro-1H-thieno [3,4-d]imidazol-4-yl)pentanamido)ethyl)amino)ethyl) amino)propyl (2-cyanoethyl) diisopropylphosphoramidite, (10). Monoprotected diol 10' (147 mg, 0.193 mmol, 1 equiv.) was suspended in acetonitrile and solvent was evaporated under reduced pressure (60° C.). The operation was repeated once and the dried compound was kept under high vacuum for at least 5 hours. In an oven-dried flask, 10' was then dissolved in anhydrous DCM (2 ml) and 0.77 ml of dry activator solution (ethylthiotetrazole, 0.25M in ACN) (0.19 mmol, 1 equiv.) was added under stirring. 2-Cyanoethyl N,N,N',N'-tetraisopropylphosphorodiamidite (0.06 ml, 0.19 mmol, 1 equiv.) was added slowly and the reaction was allowed to stir under inert gas at room temperature for 1 hour. Two fast extractions with DCM from a 10% Na$_2$CO$_3$ aqueous solution were performed. Organic fractions were combined, dried over MgSO$_4$, filtered and the solvent was evaporated under reduced pressure (40° C.). The crude product was loaded on celite and purified using the combiFlash system with a SiO2 "Gold" column pretreated with 1% TEA in DCM. DCM/TEA (100:1) and DCM/Methanol/TEA (90:10:1) were used in a gradient. Product was extracted again to remove triethylammonium salts, once with DCM from 10% Na$_2$CO$_3$ aqueous solution, washed once with a 10% Na$_2$CO$_3$ aqueous solution, dried over MgSO$_4$, filtered and solvent was evaporated under reduced pressure (60° C.). A white solid was isolated (106 mg, 0.110 mmol, 57%). HRMS (ESI-QTOF) m/z: [M+Na]+ Calcd for C$_{50}$H$_{72}$N$_7$NaO$_8$PS 984.4793; Found 984.4813. $^1$H NMR (500 MHz, CDCl$_3$): δ (ppm) 7.51-7.49 (m, 1H), 7.40-7.38 (m. 2H), 7.29-7.26 (m, 6H), 7.22-7.19 (m, 1H), 7.05-7.02 (m, 1H), 6.83-6.80 (m, 4H), 6.58 (br. s, 1H), 5.70 (br. s, 1H), 4.49-4.46 (m, 1H), 4.29-4.26 (m, 1H), 3.86-3.54 (m, 12H), 3.40-3.31 (m, 2H), 3.28-3.20 (m, 2H), 3.12-3.02 (m, 5H), 2.90-2.86 (m, 1H), 2.75-2.72 (m, 1H), 2.62-2.55 (m, 6H), 2.22-2.12 (m, 2H), 1.77-1.60 (m, 8H), 1.45-1.36 (m, 2H), 1.17 (t, J=7 Hz, 12H). $^{13}$C NMR (126 MHz, CDCl$_3$): δ (ppm) 173.6, 173.5, 164.1, 158.5, 145.2, 136.5, 130.1, 128.2, 127.9, 126.9, 117.9, 113.2, 86.0, 61.9, 61.8, 61.7, 61.5, 60.3, 58.6, 58.4, 58.2, 52.5, 52.4, 43.2, 43.1, 40.7, 40.5, 38.9, 36.1, 29.8, 29.0, 29.0, 28.2, 28.2, 27.8, 25.6, 24.8, 24.8, 20.6, 20.5. $^{31}$P NMR (203 MHz, CDCl$_3$): δ (ppm) 147.5.

General Solid-Phase Synthesis Procedure

Standard DNA synthesis was performed on a 1 μmol scale, starting from a universal 1000 Å LCAA-CPG solid support. Amidites HEG and TEG were dissolved in dry acetonitrile and all other amidites were dissolved in dry DCM to obtain 0.1M solutions. Extended coupling times of 10 minutes were used except for standard DNA amidites and for oligomer A synthesis (4 min couplings). Removal of the DMT protecting group was carried out using 3% dichloroacetic acid in dichloromethane on the DNA synthesizer. The DNA sequence used is called AT and is: 5'-TTTTTCAGTTGACCATATA-3' (SEQ ID NO: 1) except for the oligomer D for which the sequence used was 5'-CAGTTGACCATATA-3' (SEQ ID NO: 2).

General Procedure for Attaching Moiety without Phosphoramidite Isolation

Under a nitrogen atmosphere in a glove box (<2.5 ppm trace moisture), in a 20 ml oven-dried round bottom flask, monoprotected alcohol 1' (31.6 mg, 0.050 mmol) is dissolved in dry DCM (500 μl). Diisopropylethylamine (8.7 μl, 0.050 mmol, 1 equiv.) and N,N-Diisopropylamino cyanoethyl phosphonamidic-Cl (10.0 μl, 0.045 mmol, 0.9 equiv.) are added. Reaction is allowed to stir at room temperature during 45 minutes. Coupling was done using the 'syringe' technique: the crude solution containing the phosphoramidite (200 μl, 0.1 M) is mixed with the standard activator solution (200 μl, 0.25 M) in presence of the CPG using syringes. After ten minutes, the solution was removed from the columns and the strands underwent capping, oxidation and deblocking steps in the synthesizer.

General Deprotection Procedure

Sequences without moiety 4P, 5P, 8P, 9P or 11P underwent classical deprotection procedures: completed syntheses were cleaved from the solid support and deprotected in 28% aqueous ammonium hydroxide solution for 16-18 hours at 65° C. or in 28% aqueous ammonium hydroxide/30% methylamine solution 1:1 mixture for 3 h hours at 65° C. With moieties 4P, 5P, 8P, 9P, 1:3 tert-butylamine/water solution during 6 h at 65° C. (recommended with dmf-protected guanosines) or 0.4M NaOH 1:4 water/methanol solution at room temperature during 16 h, followed by quenching with 2.0M TEAA buffer (recommended with isobutyryl-protected guanosines) were used. With moiety 11P, a solution of 0.4M NaOH 1:4 water/methanol solution at 65° C. overnight, followed by quenching with 2.0M TEAA buffer could fully deprotect the tBu ester. The crude product solution was separated from the solid support and concentrated under reduced pressure at 60° C. This crude solid was re-suspended in 1 mL Millipore water. Filtration with 0.22 μm centrifugal filter was then performed prior to HPLC purification. The resulting solution was quantified by absorbance at 260 nm. NB: if 1:3 tert-butylamine/water solution during 6 h at 65° C. does not lead to complete unylinker deprotection, concentrated ammonium hydroxide at room temperature overnight could be performed as a second step.

General Procedure for RP-HPLC Purification

Solvents (0.22 μm filtered): 50 mM triethylammonium acetate (TEAA) buffer (pH 8.0) and HPLC grade acetonitrile. All gradients were followed by a short column wash in 95% acetonitrile. Column: Hamilton PRP-C18 5 μm 100 Å 2.1×150 mm. For each analytical separation approximately 0.5 OD260 of crude DNA or 0.3 OD260 of crude oligomers was injected as a 20-50 μL solution in Millipore water. Detection was carried out using a diode-array detector, monitoring absorbance at 260 nm.

Post Solid-Phase Synthesis Functionalization of Alkyne Containing DNA Strands

Two strands containing one and 5 times phosphoramidite 2 have been modified after solid-phase synthesis following a standard protocol reported elsewhere (Organic Letters, 2006, 3639-3642). With DNA-2: to 20 μL of a DNA solution (directly from post-deprotection crude 6.6 nmol) in water, 10 μL of an azide solution (164 nmol, 25 equiv.) and 10 μL of a freshly prepared solution containing CuBr and Ligand in a 1:1 ration in 4:3:1 water:DMSO:tBuOH was added (66 nmol, 10 equiv.). The mixture was vortexed and shaken at room temperature for 2 hours. With DNA-2$_5$ (oligomer E): To 20 μL of a DNA solution (directly from post-deprotection crude, 9.5 nmol) in water 10 μL of an azide solution (475 nmol, 50 equiv.) and 10 μL of a freshly prepared solution containing CuBr and Ligand in a 1:1 ration in 4:3:1 water: DMSO:tBuOH was added (180 nmol, 20 equiv.). The mixture was vortexed and shaken at room temperature for 2 hours. In the case of post-SPS click chemistry compounds, purification was carried out through gel electrophoresis instead of RP-HPLC. Crude products were purified on 20% polyacrylamide gels, supplemented with 7M urea (loading up to 10 OD260 of crude mixture per gel, 500 V field applied). Electrophoresis was run at lower voltage for the first 30 minutes. Following electrophoresis, the gel was wrapped in plastic and visualized by UV shadowing over a fluorescent TLC plate. The full-length product was quickly excised, then crushed and incubated in ~10 mL of Millipore water. The solution was frozen in liquid N$_2$ for 3 minutes and left at 65° C. overnight. The supernatant was then concentrated to 1.0 mL, and desalted using size exclusion chromatography (Sephadex G-25). The DNA strand was then quantified (OD260) and converted to micromolar concentrations using the calculated extinction coefficient.

Two strands containing phosphoramidite 2 at different positions have been modified with a sulfonated dye azide purchased from Sigma following a procedure reported elsewhere (Hong, et al., Angew. Chem. Int. Ed. 2009, 48, 9879).

While the disclosure has been described in connection with specific embodiments thereof, it will be understood that it is capable of encompassing further modifications and this application is intended to cover any variations, uses, or adaptations, including such departures from the present disclosure as come within known or customary practice within the art to which and as may be applied to the essential features hereinbefore set forth, and as follows in the scope of the appended claims.

What is claimed is:

1. A reagent having the following structure

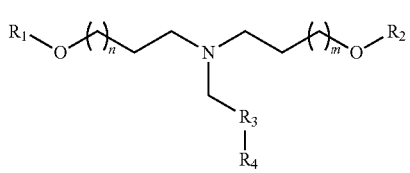

wherein:
R1 is dimethoxytrityl (DMT), monomethoxytrityl (MMT), or other hydroxyl protecting group stable to oligonucleotide synthesis conditions;
R2 is a -phosphoramidityl residue

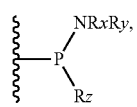

wherein Rx and Ry are independently selected from the group consisting of C1-10 branched alkyl, C1-12 alkyl, and cyclic hydrocarbyls; and Rz is a phosphite-protecting group; or
R2 is H,
R3 and R4 together form an alkyl, ethynyl or propargyl residue; or
R3 is:
a homo or heteroarylene residue

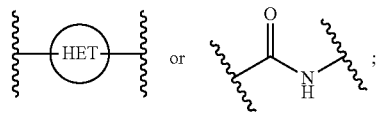

or R3 is an alkyl or oligo(ethylene glycol) chain with an amide or a heteroarylene residue on which is attached R4,
R4 is:
an optionally protected amino-acid or short peptide covalently attached to said R3;
a diaminoalkyl residue of general formula

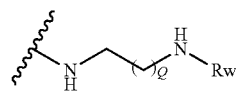

wherein Rw is an amino protecting group; or
an optionally protected monosaccharide residue covalently attached to R3; or
a fluorophore, biotin, a strained alkyne, a disulfide, a protected thiol, a cross-linker or folic acid having suitable protecting groups,
n is an integer of 1 to 4,
m is an integer of 1 to 4, and
Q is an integer greater than 1.

2. The reagent of claim 1, wherein Rx and Ry are CH(CH₃)₂ and Rz is O—(CH₂)₂—CN.

3. The reagent of claim 1, wherein R1 is dimethoxytrityl (DMT).

4. The reagent of claim 1, wherein R3 is:

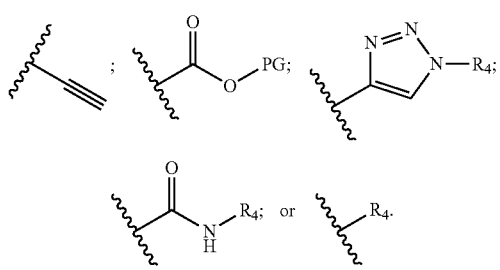

5. The reagent of claim 1, wherein R4 is:

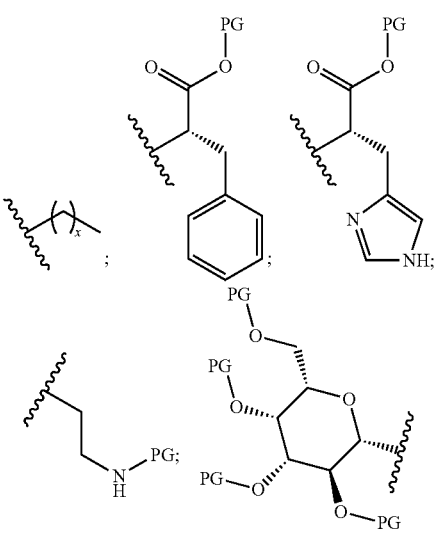

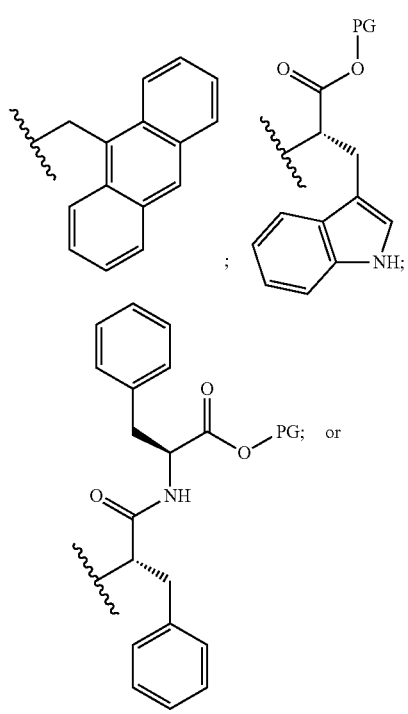

-continued

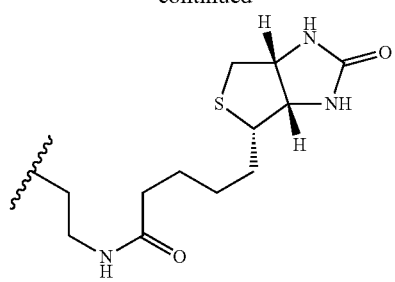

wherein PG is a protecting group.

6. The reagent of claim 1, further comprising an amine functionalized with a carboxylic acid.

7. The reagent of claim 6, wherein the amine is functionalized with an amino acid, a carbohydrate, a short peptide, a fluorophore, biotin, a strained alkyne, a disulfide, a protected thiol, a cross-linker or folic acid having suitable protecting groups.

8. The reagent of claim 5, wherein the protecting group is an ester group or an acetate group.

9. The reagent of claim 5, wherein the protecting group is, a silylated group, a trifluoroacetate group, a fluorenylmethyloxycarbonyl (FMOC) group, a monomethoxytrityl group, a 4-tertbutylbenzoyl group, a trityl group, an isobutyrate group, a trifluoroacetic acid (TFA) group or a methyl ester group.

10. The reagent of claim 1, having the following structures:

1

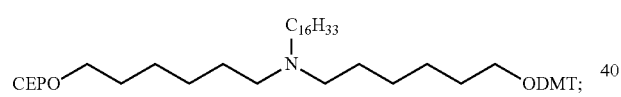

2

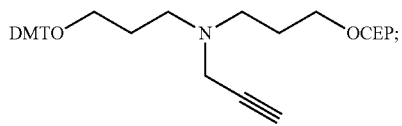

3

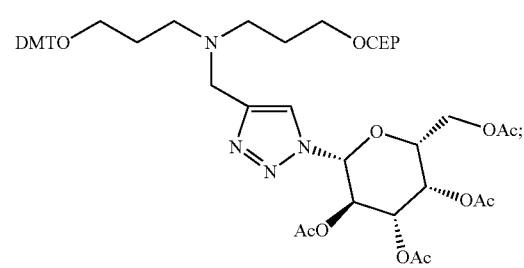

4

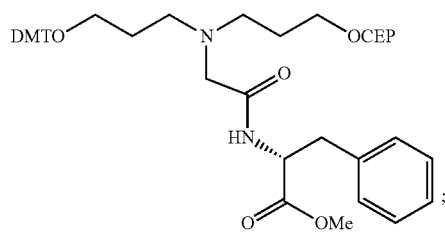

5

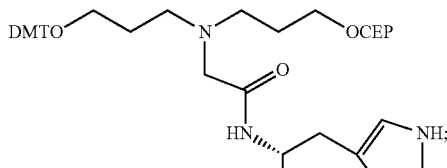

6

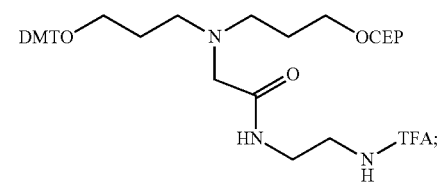

7

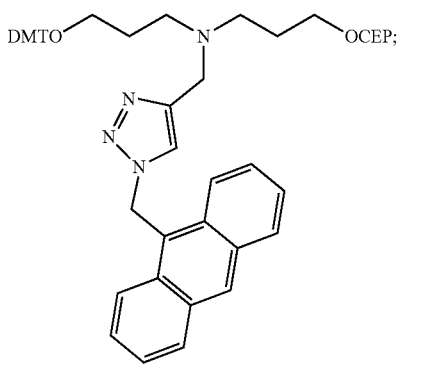

8

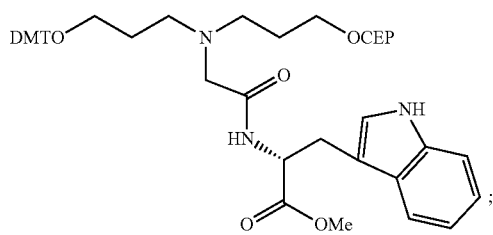

9

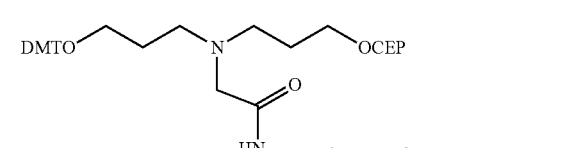

; or

10

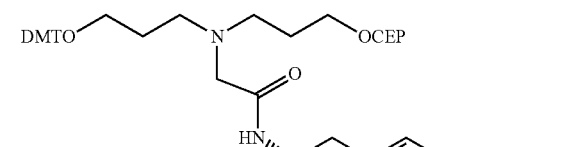

11. A process to modify a synthetic oligonucleotide and/or to make a sequence-controlled oligomer, at any positions wherein the process comprises covalently attaching the reagent as defined in claim 1, into said oligonucleotide and/or sequence-controlled oligomer by performing a phosphoramidite coupling during a synthesis of said oligonucleotide and/or sequence-controlled oligomer.

12. The process of claim 11, further comprising the step of functionalizing the oligonucleotide and/or sequence-controlled oligomer using click chemistry.

13. The process of claim 12, wherein the oligonucleotide and/or sequence-controlled oligomer is functionalized with a fluorophore, biotin, a strained alkyne, a disulfide, a protected thiol, a cross-linker or folic acid having suitable protecting groups.

14. The process of claim 13, wherein the dye is a Cy5 sulfonated dye.

15. The process of claim 11, wherein the synthetic oligonucleotide and/or sequence-controlled oligomer is modified or made in an automated synthesizer.

* * * * *